(12) United States Patent
Asaoka et al.

(10) Patent No.: US 10,611,817 B2
(45) Date of Patent: Apr. 7, 2020

(54) FC-BINDING PROTEIN, METHOD FOR PRODUCING SAID PROTEIN, AND ANTIBODY ADSORBENT USING SAID PROTEIN, AND METHODS FOR PURIFYING AND IDENTIFYING ANTIBODY USING SAID ADSORBENT

(71) Applicant: TOSOH CORPORATION, Yamaguchi (JP)

(72) Inventors: Yoshiharu Asaoka, Kanagawa (JP); Toru Tanaka, Kanagawa (JP); Teruhiko Ide, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 300 days.

(21) Appl. No.: 15/022,130

(22) PCT Filed: Sep. 18, 2014

(86) PCT No.: PCT/JP2014/074739
§ 371 (c)(1),
(2) Date: Mar. 15, 2016

(87) PCT Pub. No.: WO2015/041303
PCT Pub. Date: Mar. 26, 2015

(65) Prior Publication Data
US 2016/0222081 A1    Aug. 4, 2016

(30) Foreign Application Priority Data

| Sep. 18, 2013 | (JP) | 2013-192931 |
| Sep. 27, 2013 | (JP) | 2013-202245 |
| Aug. 19, 2014 | (JP) | 2014-166883 |
| Aug. 19, 2014 | (JP) | 2014-166884 |

(51) Int. Cl.
| C07K 1/00 | (2006.01) |
| C07H 21/04 | (2006.01) |
| C12P 21/06 | (2006.01) |
| C12P 21/04 | (2006.01) |
| C12N 5/00 | (2006.01) |
| C12N 1/20 | (2006.01) |
| C12N 15/00 | (2006.01) |
| C07K 14/735 | (2006.01) |
| C07K 1/22 | (2006.01) |
| C07K 17/00 | (2006.01) |
| C07H 1/06 | (2006.01) |
| C07K 16/28 | (2006.01) |
| C07K 16/00 | (2006.01) |

(52) U.S. Cl.
CPC .......... *C07K 14/70535* (2013.01); *C07H 1/06* (2013.01); *C07K 1/22* (2013.01); *C07K 16/283* (2013.01); *C07K 17/00* (2013.01); *C07K 2317/10* (2013.01); *C07K 2317/732* (2013.01)

(58) Field of Classification Search
None
See application file for complete search history.

(56) References Cited

U.S. PATENT DOCUMENTS

| 6,444,789 B1 | 9/2002 | Luo | |
| 6,737,056 B1 * | 5/2004 | Presta | C07K 16/4291 424/133.1 |
| 2007/0207163 A1 | 9/2007 | Sondermann et al. | |
| 2013/0079499 A1 | 3/2013 | Hatayama et al. | |
| 2017/0218044 A1 | 8/2017 | Asaoka et al. | |

FOREIGN PATENT DOCUMENTS

| WO | 96/34953 | 11/1996 |
| WO | 00/32767 | 6/2000 |
| WO | 03/054213 | 7/2003 |
| WO | 2003/054213 | 7/2003 |
| WO | 2004/062619 | 7/2004 |
| WO | 2013/013193 | 1/2013 |
| WO | 2015/199154 | 12/2015 |

OTHER PUBLICATIONS

Ellsworth et al., "Generation of a High-Affinity Fcγ Receptor by Ig-Domain Swapping Between Human CD64A and CD16A," *Protein Engineering, Design & Selection*, vol. 23, No. 4, pp. 299-309, 2010.

Ferrara et al., "The Carbohydrate at FcγRIIIa Asn-162: An Element Required for High Affinity Binding to Non-Fucosylated IgG Glycoforms," *The Journal of Biological Chemistry*, vol. 281, No. 8, pp. 5032-5036, Feb. 24, 2006.

Galon et al., "Affinity of the Interaction Between Fc Gamma Receptor Type III (FcγRIII) and Monomeric Human IgC Subclasses. Role of FcγRIII Glycosylation," *Eur. J. Immunol.*, vol. 27, pp. 1928-1932, 1997.

(Continued)

*Primary Examiner* — Chun W Dahle
(74) *Attorney, Agent, or Firm* — Greenblum & Bernstein, P.L.C.

(57) ABSTRACT

The present invention addresses the first problem of providing an Fc-binding protein having improved stability, especially stability to heat and acid, of the Fc-binding protein, a method for producing this protein, and an antibody adsorbent using this protein. The present invention also addresses the second problem of providing a method that makes it possible to identify the presence or absence of glycosylation of an antibody, and a material to be used in this method. The first problem is solved by an Fc-binding protein having improved stability to heat and acid obtained by substituting amino acid residues at specific positions in the extracellular domain within human FcγRIIIa with other specific amino acids, a method for producing this protein, and an antibody adsorbent using this protein. The second problem is solved by using an adsorbent capable of specifically adsorbing an antibody having a sugar chain, the adsorbent being obtained by immobilizing human FcγRIIIa on an insoluble carrier.

17 Claims, 7 Drawing Sheets

Specification includes a Sequence Listing.

(56) References Cited

OTHER PUBLICATIONS

Shibata-Koyama et al., "The N-linked Ogliosaccharide at FcγRIIIa Asn-45: An Inhibitory Element for High FcγRIIIa Binding Affinity to IgG Glycoforms Lacking Core Fucosylation," *Glycobiology* vol. 19, No. 2, pp. 126-134, 2009.
Shinkawa et al., "The Absence of Fucose but Note the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, vol. 278, No. 5, pp. 3466-3473, 2003.
Takai, "Role of Fcγ Receptors in Immune Regulation and Diseases," *Jpn. J. Clin. Immunol.*, vol. 28, No. 5, pp. 318-326, 2005.
Zou et al., "Chemoenzymatic Synthesis and Fcγ Receptor Binding of Homogeneous Glycoforms of Antibody Fc Domain. Presence of a Bisecting Sugar Moiety Enhances the Affinity of Fc to FcγIIIa Receptor," *Journal of the American Chemical Society*, vol. 133, No. 46, pp. 18975-18991, Nov. 23, 2011.
Rogers et al., "IgG Fc Receptor III Homologues in Nonhuman Primate Species: Genetic Characterization and Ligand Interactions," *J. Immunol.*, vol. 177, No. 6, pp. 3848-3856, Sep. 15, 2006.
International Search Report issued in PCT/JP2014/074739, dated Dec. 22, 2014.
K. A. Rogers et al., "IgG Fc Receptor III Homologues in Nonhuman Primate Species: Genetic Characterizaiton and Ligan Interactions", The Journal of Immunology, vol. 177, No. 6, XP055248767; Sep. 15, 2006; pp. 3848-3856.
Guozhang Zou et al., "Chemoenzymatic Synthesis and Fcγ Receptor Binding of Homogeneous Glycoforms of Antibody Fc Domain. Presence of a Bisecting Sugar Moiety Enhances the Affinity of Fc to FcγIIIa Receptor", Journal of the American Chemical, vol. 133; Nov. 23, 2011; pp. 18975-18991.
M. Shibata-Koyama et al., "The N-linked oligosaccharide at Fcγ RIIIa Asn-45: an inhibitory element for high Fcγ RIIIa binding affinity to IgG glycoforms lacking core fucosylation ", Glycobiology, vol. 19, No. 2, XP055332309; Oct. 24, 2008; pp. 126-134.
J. L. Ellsworth et al., "Generation of a high-affinity Fcγ receptor by Ig-domain swapping between human CD64A and CD16A", Protein Engineering, Design & Selection, vol. 23, No. 4, XP055332310; Feb. 11, 2010; pp. 299-309.
Claudia Ferrara et al., "The carbohydrate at FcγRIIIa Asn-162 an Element Required for High Affinity Binding to Non-Fucosylated IgG Glycoforms", Journal of Biological Chemistry American Society for Biochemistry and Molecular Biology, US, vol. 281, No. 8, XP002430982; Feb. 24, 2006; pp. 5032-5036.
Database UniProt[Online] Oct. 19, 2011, "SubName: Full= Uncharacterized protein{ECO:0000313| Ensembl: ENSNLEP00000017512};", XP002770838, retrieved from EBI accession No. UNIPROT: G1RW85 Database accession No. G1RW85.
Database UniProt[Online] Jul. 27, 2011, "SubName: Full= Uncharacterized protein{ECO:0000313| Ensembl: ENSCJA00000008582};", XP002770839, retrieved from EBI accession No. UNIPROT: F7IPS7 Database accession No. F7IPS7.
M. L. Hibbs et al., "Membrane-Proximal Ig-like Domain of FcgγRIII (CD16) Containes Residues Critical for Ligand Binding", The Journal of Immunology, The America Association of Immunologists, US, vol. 152, XP000647749; May 1, 1994; pp. 4466-4474.
M. Kiyoshi, et al., "Structural Basis for Binding of Human IgG1 to its High-Affinity Human Receptor FcgammaRI," Nature Communications, 6:6866; pp. 1-11, published Apr. 30, 2015.

\* cited by examiner

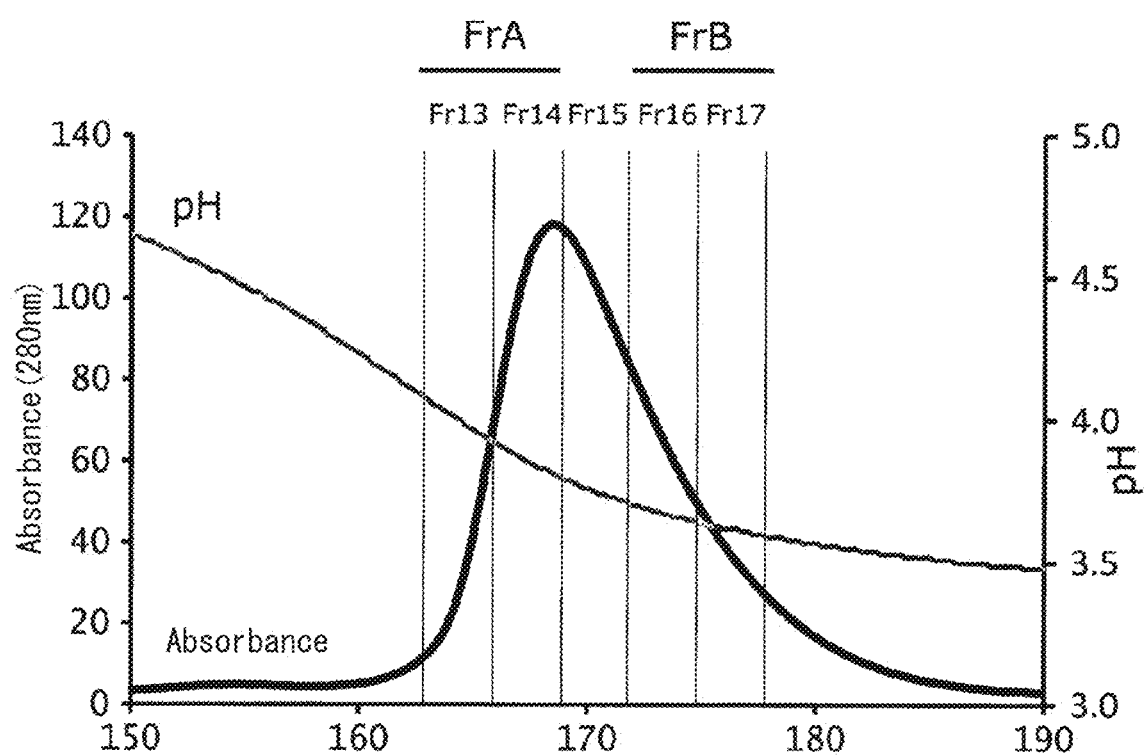

FIG. 5

| | Expected sugar chain structures |
|---|---|
| N1 | GlcNAcβ1-2Manα1-6 \ <br>                        Manβ1-4GlcNAcβ1-4GlcNAc-PA <br> GlcNAcβ1-2Manα1-3 / |
| N2 | Galβ1-4GlcNAcβ1-2Manα1-6 \ <br>                            Manβ1-4GlcNAcβ1-4GlcNAc-PA <br> GlcNAcβ1-2Manα1-3 / |
| N3 | GlcNAcβ1-2Manα1-6 \      Fucα1-6 \ <br>                      Manβ1-4GlcNAcβ1-4GlcNAc-PA <br> GlcNAcβ1-2Manα1-3 / |
| N4 | Galβ1-4GlcNAcβ1-2Manα1-6 \      Fucα1-6 \ <br>                            Manβ1-4GlcNAcβ1-4GlcNAc-PA <br> GlcNAcβ1-2Manα1-3 / |
| N5 | GlcNAcβ1-2Manα1-6 \      Fucα1-6 \ <br>                       Manβ1-4GlcNAcβ1-4GlcNAc-PA <br> Galβ1-GlcNAcβ1-2Manα1-3 / |
| N6 | Galβ1-GlcNAcβ1-2Manα1-6 \      Fucα1-6 \ <br>                          Manβ1-4GlcNAcβ1-4GlcNAc-PA <br> Galβ1-GlcNAcβ1-2Manα1-3 / |
| N7 | GlcNAcβ1-2Manα1-6 \      Fucα1-6 \ <br>                    GlcNAcβ1-4-Manβ1-4GlcNAcβ1-4GlcNAc-PA <br> GlcNAcβ1-2Manα1-3 / |
| N8 | Galβ1-GlcNAcβ1-2Manα1-6 \      Fucα1-6 \ <br>                       GlcNAcβ1-4-Manβ1-4GlcNAcβ1-4GlcNAc-PA <br> GlcNAcβ1-2Manα1-3 / |
| M1 | GlcNAcβ1-2Manα1-6 \      Fucα1-6 \ <br>                                    Manβ1-4GlcNAcβ1-4GlcNAc-PA <br> Neu5Acα2-6Galβ1-4GlcNAcβ1-2Manα1-3 / |
| M2 | Galβ1-4GlcNAcβ1-2Manα1-6 \      Fucα1-6 \ <br>                                      Manβ1-4GlcNAcβ1-4GlcNAc-PA <br> Neu5Acα2-6Galβ1-4GlcNAcβ1-2Manα1-3 / |

FIG. 8
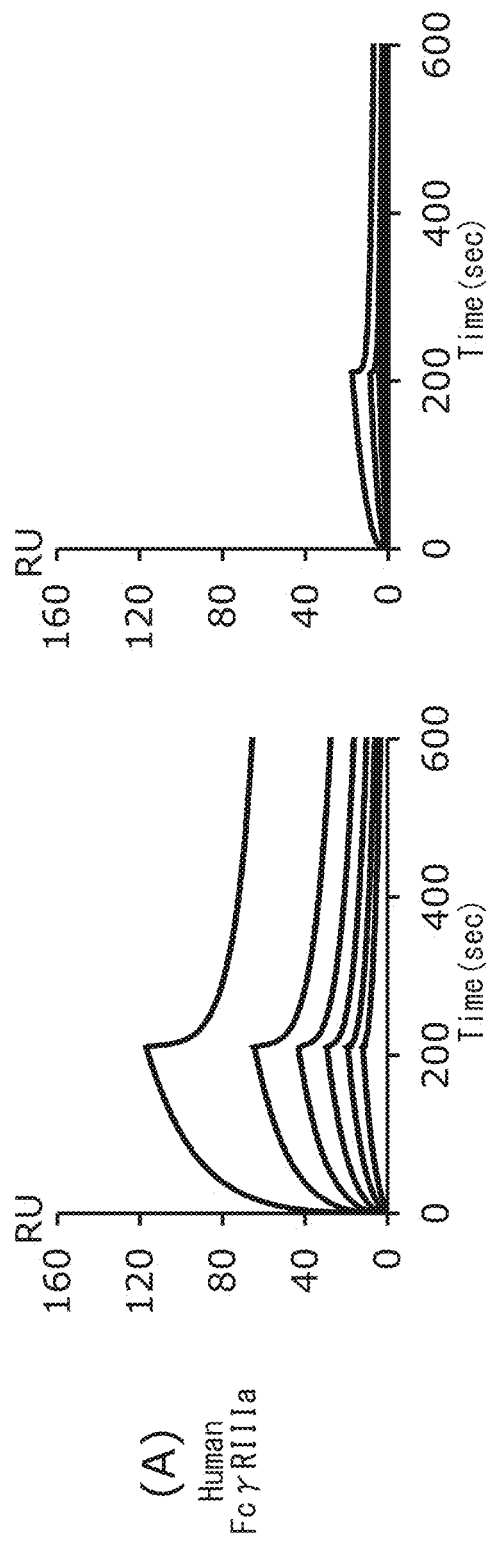
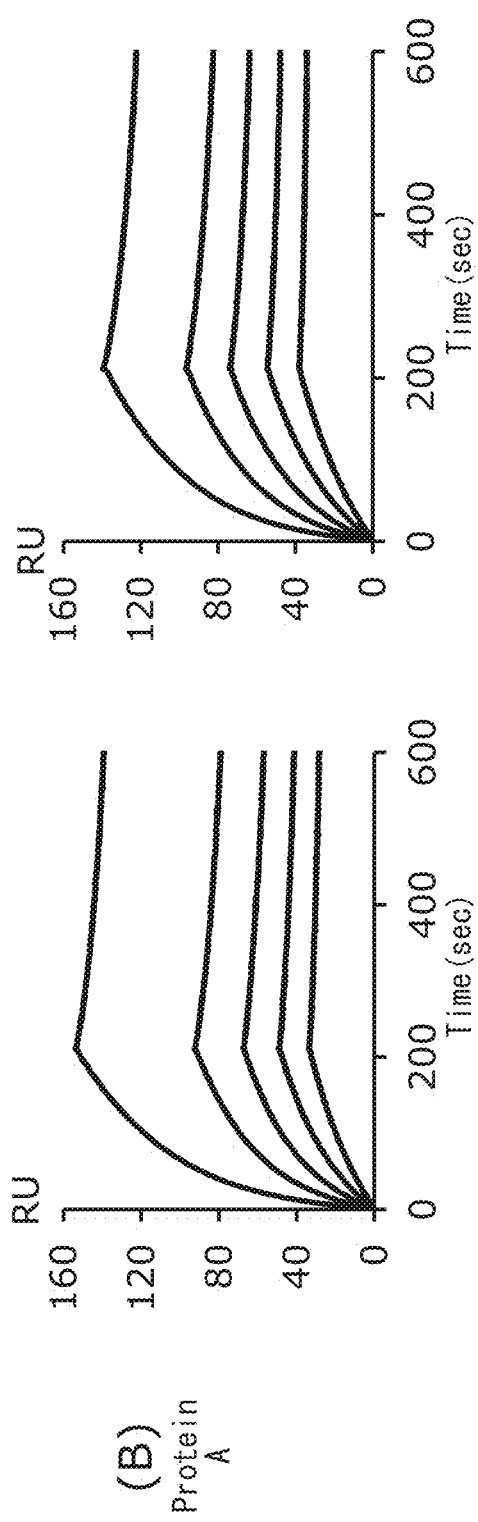

SEQUENCE LISTING

```
<160> NUMBER OF SEQ ID NOS: 56

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30
```

| | | | | | | | | | | | | |
|---|---|---|---|---|---|---|---|---|---|---|---|---|
|Gln|Trp|Tyr|Arg|Val|Leu|Glu|Lys|Asp|Ser|Val|Thr|Leu|Lys|Cys|Gln|
| | |35| | | |40| | | |45| | | | | |

Gln Trp Tyr Arg Val Leu Glu Lys Asp Ser Val Thr Leu Lys Cys Gln
              35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 528
<212> TYPE: DNA
<213> ORGANISM: Artificial Sequence
<220> FEATURE:
<223> OTHER INFORMATION: E.coli codon CD16a

<400> SEQUENCE: 2

```
ggcatgcgta ccgaagatct gccgaaagcg gtggtgtttc tggaaccgca gtggtatcgc      60
gtgctggaga aagattctgt gaccctaaa tgccagggcg cgtatagccc ggaagataac     120
agcacccagt ggttccacaa tgaaagcctg atttccagcc aggcgagcag ctactttatt     180
gatgcggcga cggtggatga tagcggcgaa tatcgttgcc agaccaacct gagcaccctg     240
agcgatccgg tgcagctgga ggtgcacatc gggtggcttc tgttacaggc tccacggtgg     300
gtgttcaaag aggaggatcc gattcatctg cggtgtcact cctggaagaa taccgccctg     360
cataaagtga cctacctgca aaacggcaag ggccgcaagt atttccacca caactccgac     420
ttctatattc ccaaagcgac gctgaaggac agcggcagct atttctgccg tgggctggtg     480
ggcagcaaaa atgtgagcag cgagaccgtg aatattacca ttacccaa              528
```

<210> SEQ ID NO 3
<211> LENGTH: 41
<212> TYPE: DNA
<213> ORGANISM: Artificial sequence
<220> FEATURE:
<223> OTHER INFORMATION: Oligonucleotide

<400> SEQUENCE: 3
ggcatgcgta ccgaagatct gccgaaagcg gtggtgtttc t                    41

<210> SEQ ID NO 4
<211> LENGTH: 48
<212> TYPE: DNA
<213> ORGANISM: Artificial sequence
<220> FEATURE:
<223> OTHER INFORMATION: Oligonucleotide

<400> SEQUENCE: 4
tctccagcac gcgataccac tgcggttcca gaaacaccac cgctttcg             48

<210> SEQ ID NO 5
<211> LENGTH: 48
<212> TYPE: DNA
<213> ORGANISM: Artificial sequence
<220> FEATURE:
<223> OTHER INFORMATION: Oligonucleotide

<400> SEQUENCE: 5
ggtatcgcgt gctggagaaa gattctgtga cccttaaatg ccagggcg             48

<210> SEQ ID NO 6
<211> LENGTH: 48
<212> TYPE: DNA
<213> ORGANISM: Artificial sequence
<220> FEATURE:
<223> OTHER INFORMATION: Oligonucleotide

<400> SEQUENCE: 6
actgggtgct gttatcttcc gggctatacg cgccctggca tttaaggg             48

<210> SEQ ID NO 7
<211> LENGTH: 48
<212> TYPE: DNA
<213> ORGANISM: Artificial sequence
<220> FEATURE:
<223> OTHER INFORMATION: Oligonucleotide

<400> SEQUENCE: 7
ggaagataac agcacccagt ggttccacaa tgaaagcctg atttccag             48

<210> SEQ ID NO 8
<211> LENGTH: 48
<212> TYPE: DNA
<213> ORGANISM: Artificial sequence
<220> FEATURE:
<223> OTHER INFORMATION: Oligonucleotide

<400> SEQUENCE: 8
catcaataaa gtagctgctc gcctggctgg aaatcaggct ttcattgt             48

<210> SEQ ID NO 9
<211> LENGTH: 48
<212> TYPE: DNA
<213> ORGANISM: Artificial sequence
<220> FEATURE:
<223> OTHER INFORMATION: Oligonucleotide

<400> SEQUENCE: 9
gcgagcagct actttattga tgcggcgacg gtggatgata gcggcgaa             48

```
<210> SEQ ID NO 10
<211> LENGTH: 48
<212> TYPE: DNA
<213> ORGANISM: Artificial sequence
<220> FEATURE:
<223> OTHER INFORMATION: Oligonucleotide

<400> SEQUENCE: 10
cagggtgctc aggttggtct ggcaacgata ttcgccgcta tcatccac          48

<210> SEQ ID NO 11
<211> LENGTH: 48
<212> TYPE: DNA
<213> ORGANISM: Artificial sequence
<220> FEATURE:
<223> OTHER INFORMATION: Oligonucleotide

<400> SEQUENCE: 11
accaacctga gcaccctgag cgatccggtg cagctggagg tgcacatc           48

<210> SEQ ID NO 12
<211> LENGTH: 48
<212> TYPE: DNA
<213> ORGANISM: Artificial sequence
<220> FEATURE:
<223> OTHER INFORMATION: Oligonucleotide

<400> SEQUENCE: 12
ccaccgtgga gcctgtaaca gaagccaccc gatgtgcacc tccagctg           48

<210> SEQ ID NO 13
<211> LENGTH: 48
<212> TYPE: DNA
<213> ORGANISM: Artificial sequence
<220> FEATURE:
<223> OTHER INFORMATION: Oligonucleotide

<400> SEQUENCE: 13
agggcggtat tcttccagga gtgacaccgc agatgaatcg gatcctcc           48

<210> SEQ ID NO 14
<211> LENGTH: 48
<212> TYPE: DNA
<213> ORGANISM: Artificial sequence
<220> FEATURE:
<223> OTHER INFORMATION: Oligonucleotide

<400> SEQUENCE: 14
cctggaagaa taccgccctg cataaagtga cctacctgca aaacggca           48

<210> SEQ ID NO 15
<211> LENGTH: 48
<212> TYPE: DNA
<213> ORGANISM: Artificial sequence
<220> FEATURE:
<223> OTHER INFORMATION: Oligonucleotide

<400> SEQUENCE: 15
cggagttgtg gtggaaatac ttgcggccct tgccgttttg caggtagg           48

<210> SEQ ID NO 16
<211> LENGTH: 48
<212> TYPE: DNA
<213> ORGANISM: Artificial sequence
<220> FEATURE:
<223> OTHER INFORMATION: Oligonucleotide
```

<400> SEQUENCE: 16
agtatttcca ccacaactcc gacttctata ttcccaaagc gacgctga        48

<210> SEQ ID NO 17
<211> LENGTH: 48
<212> TYPE: DNA
<213> ORGANISM: Artificial sequence
<220> FEATURE:
<223> OTHER INFORMATION: Oligonucleotide

<400> SEQUENCE: 17
agcccacggc agaaatagct gccgctgtcc ttcagcgtcg ctttggga        48

<210> SEQ ID NO 18
<211> LENGTH: 48
<212> TYPE: DNA
<213> ORGANISM: Artificial sequence
<220> FEATURE:
<223> OTHER INFORMATION: Oligonucleotide

<400> SEQUENCE: 18
ctatttctgc cgtgggctgg tgggcagcaa aaatgtgagc agcgagac        48

<210> SEQ ID NO 19
<211> LENGTH: 43
<212> TYPE: DNA
<213> ORGANISM: Artificial sequence
<220> FEATURE:
<223> OTHER INFORMATION: Oligonucleotide

<400> SEQUENCE: 19
ttgggtaatg gtaatattca cggtctcgct gctcacattt ttg            43

<210> SEQ ID NO 20
<211> LENGTH: 48
<212> TYPE: DNA
<213> ORGANISM: Artificial sequence
<220> FEATURE:
<223> OTHER INFORMATION: Oligonucleotide

<400> SEQUENCE: 20
tacaggctcc acggtgggtg ttcaaagagg aggatccgat tcatctgc        48

<210> SEQ ID NO 21
<211> LENGTH: 37
<212> TYPE: DNA
<213> ORGANISM: Artificial sequence
<220> FEATURE:
<223> OTHER INFORMATION: Oligonucleotide

<400> SEQUENCE: 21
tagccatggg catgcgtacc gaagatctgc cgaaagc                   37

<210> SEQ ID NO 22
<211> LENGTH: 66
<212> TYPE: DNA
<213> ORGANISM: Artificial sequence
<220> FEATURE:
<223> OTHER INFORMATION: Oligonucleotide

<400> SEQUENCE: 22
cccaagctta atgatgatga tgatgatggc ccccttgggt aatggtaata ttcacggtct    60
cgctgc                                                              66

```
<210> SEQ ID NO 23
<211> LENGTH: 20
<212> TYPE: DNA
<213> ORGANISM: Artificial sequence
<220> FEATURE:
<223> OTHER INFORMATION: Sequence primer

<400> SEQUENCE: 23
taatacgact cactataggg                                              20

<210> SEQ ID NO 24
<211> LENGTH: 19
<212> TYPE: DNA
<213> ORGANISM: Artificial sequence
<220> FEATURE:
<223> OTHER INFORMATION: Sequence primer

<400> SEQUENCE: 24
tatgctagtt attgctcag                                               19

<210> SEQ ID NO 25
<211> LENGTH: 216
<212> TYPE: PRT
<213> ORGANISM: Artificial Sequence
<220> FEATURE:
<223> OTHER INFORMATION: MalE-CD16a-6His

<400> SEQUENCE: 25
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Val Val Phe Leu Glu Pro
        35                  40                  45

Gln Trp Tyr Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Phe Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Glu Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His
    210                 215

<210> SEQ ID NO 26
<211> LENGTH: 648
<212> TYPE: DNA
<213> ORGANISM: Artificial sequence
<220> FEATURE:
<223> OTHER INFORMATION: pET-eFcR

<400> SEQUENCE: 26

```
atgaaaataa aaacaggtgc acgcatcctc gcattatccg cattaacgac gatgatgttt      60
tccgcctcgg ctctcgccaa atcgaagaa gccatgggca tgcgtaccga agatctgccg      120
aaagcggtgg tgtttctgga accgcagtgg tatcgcgtgc tggagaaaga ttctgtgacc      180
cttaaatgcc agggcgcgta tagcccggaa gataacagca cccagtggtt ccacaatgaa      240
agcctgattt ccagccaggc gagcagctac tttattgatg cggcgacggt ggatgatagc      300
ggcgaatatc gttgccagac caacctgagc accctgagcg atccggtgca gctggaggtg      360
cacatcgggt ggcttctgtt acaggctcca cggtgggtgt tcaaagagga ggatccgatt      420
catctgcggt gtcactcctg gaagaatacc gccctgcata agtgaccta cctgcaaaac      480
ggcaagggcc gcaagtattt ccaccacaac tccgacttct atattcccaa agcgacgctg      540
aaggacagcg gcagctattt ctgccgtggg ctggtgggca gcaaaaatgt gagcagcgag      600
accgtgaata ttaccattac ccaaggggc catcatcatc atcatcat      648
```

<210> SEQ ID NO 27
<211> LENGTH: 216
<212> TYPE: PRT
<213> ORGANISM: Artificial sequence
<220> FEATURE:
<223> OTHER INFORMATION: FcR2

<400> SEQUENCE: 27

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Phe Leu Glu Pro
            35                  40                  45

Gln Trp Asn Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Phe Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Glu Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

```
Gly Ser Lys Asn Val Ser Ser Glu Thr Val Asn Ile Thr Ile Thr Gln
        195                 200                 205

Gly Gly His His His His His His
        210                 215

<210> SEQ ID NO 28
<211> LENGTH: 648
<212> TYPE: DNA
<213> ORGANISM: Artificial sequence
<220> FEATURE:
<223> OTHER INFORMATION: FcR2

<400> SEQUENCE: 28
atgaaaataa aaacaggtgc acgcatcctc gcattatccg cattaacgac gatgatgttt      60
tccgcctcgg ctctcgccaa atcgaagaa gccatgggca tgcgtaccga agatctgccg       120
aaagcggagg tgtttctgga accgcagtgg aatcgcgtgc tggagaaaga ttctgtgacc      180
cttaaatgcc agggcgcgta tagcccggaa gataacagca cccagtggtt ccacaatgaa      240
agcctgattt ccagccaggc gagcagctac tttattgatg cggcgacggt ggatgatagc      300
ggcgaatatc gttgccagac caacctgagc accctgagcg atccggtgca gctggaggtg      360
cacatcgggt ggcttctgtt acaggctcca cggtgggtgt tcaaagagga ggatccgatt      420
catctgcggt gtcactcctg gaagaatacc gccctgcata agtgaccta cctgcaaaac       480 ggcaagggcc gcaagtattt ccaccataac tccgacttct atattcccaa agcgacgctg      540
aaggacagcg gcagctattt ctgccgtggg ctggtgggca gcaaaaatgt gagcagcgag      600
accgtgaata ttaccattac ccaagggggc catcatcatc atcatcat                   648

<210> SEQ ID NO 29
<211> LENGTH: 30
<212> TYPE: DNA
<213> ORGANISM: Artificial sequence
<220> FEATURE:
<223> OTHER INFORMATION: Oligonucleotide

<400> SEQUENCE: 29
agccaggcga gcagctacct tattgatgcg                                        30

<210> SEQ ID NO 30
<211> LENGTH: 30
<212> TYPE: DNA
<213> ORGANISM: Artificial sequence
<220> FEATURE:
<223> OTHER INFORMATION: Oligonucleotide

<400> SEQUENCE: 30
ccaccgtcgc cgcatcaata aggtagctgc                                        30

<210> SEQ ID NO 31
<211> LENGTH: 216
<212> TYPE: PRT
<213> ORGANISM: Artificial sequence
<220> FEATURE:
<223> OTHER INFORMATION: FcR3

<400> SEQUENCE: 31

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30
```

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
 50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Tyr Leu Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
            115                 120                 125

Ala Pro Arg Trp Val Phe Lys Glu Glu Asp Pro Ile His Leu Arg Cys
        130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 32
<211> LENGTH: 648
<212> TYPE: DNA
<213> ORGANISM: Artificial sequence
<220> FEATURE:
<223> OTHER INFORMATION: FcR3

<400> SEQUENCE: 32
atgaaaataa aaacaggtgc acgcatcctc gcattatccg cattaacgac gatgatgttt        60
tccgcctcgg ctctcgccaa atcgaagaa gccatgggca tgcgtaccga agatctgccg        120
aaagcggagg tgtttctgga accgcagtgg aatcgcgtgc tggagaaaga ttctgtgacc        180
cttaaatgcc agggcgcgta tagcccggaa gataacagca cccagtggtt ccacaatgaa        240
agcctgattt ccagccaggc gagcagctac cttattgatg cggcgacggt ggatgatagc        300
ggcgaatatc gttgccagac caacctgagc accctgagcg atccggtgca gctggaggtg        360
cacatcgggt ggcttctgtt acaggctcca cggtgggtgt tcaaagagga ggatccgatt        420
catctgcggt gtcactcctg gaagaatacc gccctgcata agtgacctac ctgcaaaac        480 ggcaagggcc gcaagtattt ccaccataac tccgacttct atattcccaa agcgacgctg        540
aaggacagcg gcagctattt ctgccgtggg ctggtgggca gcaaaaatgt gagcagcgag        600
accgtgaata ttaccattac ccaagggggc catcatcatc atcatcat        648

<210> SEQ ID NO 33
<211> LENGTH: 216
<212> TYPE: PRT
<213> ORGANISM: Artificial sequence
<220> FEATURE:
<223> OTHER INFORMATION: FcR4

<400> SEQUENCE: 33

```
Met Lys Ile Lys Thr Gly Ala Arg Ile Leu Ala Leu Ser Ala Leu Thr
1               5                   10                  15
Thr Met Met Phe Ser Ala Ser Ala Leu Ala Lys Ile Glu Glu Ala Met
                20                  25                  30
Gly Met Arg Thr Glu Asp Leu Pro Lys Ala Glu Val Phe Leu Glu Pro
            35                  40                  45
Gln Trp Asn Arg Val Leu Glu Lys Asp Ser Val Thr Leu Lys Cys Gln
    50                  55                  60
Gly Ala Tyr Ser Pro Glu Asp Asn Ser Thr Gln Trp Phe His Asn Glu
65                  70                  75                  80
Ser Leu Ile Ser Ser Gln Ala Ser Ser Tyr Leu Ile Asp Ala Ala Thr
                85                  90                  95
Val Asp Asp Ser Gly Glu Tyr Arg Cys Gln Thr Asn Leu Ser Thr Leu
            100                 105                 110
Ser Asp Pro Val Gln Leu Glu Val His Ile Gly Trp Leu Leu Leu Gln
        115                 120                 125
Ala Pro Arg Trp Val Phe Lys Glu Gly Asp Pro Ile His Leu Arg Cys
    130                 135                 140
His Ser Trp Lys Asn Thr Ala Leu His Lys Val Thr Tyr Leu Gln Asn
145                 150                 155                 160
Gly Lys Gly Arg Lys Tyr Phe His His Asn Ser Asp Phe Tyr Ile Pro
                165                 170                 175
Lys Ala Thr Leu Lys Asp Ser Gly Ser Tyr Phe Cys Arg Gly Leu Val
            180                 185                 190
Gly Ser Lys Asn Val Ser Ser Glu Thr Val Asn Ile Thr Ile Thr Gln
        195                 200                 205
Gly Gly His His His His His His
    210                 215
```

<210> SEQ ID NO 34
<211> LENGTH: 648
<212> TYPE: DNA
<213> ORGANISM: Artificial sequence
<220> FEATURE:
<223> OTHER INFORMATION: FcR4

<400> SEQUENCE: 34

```
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgtttctgga accgcagtgg aatcgcgtgc tggagaaaga ttctgtgacc     180
cttaaatgcc agggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac caacctgagc accctgagcg atccggtgca gctggaggtg     360
cacatcgggt ggcttctgtt acaggctcca cggtgggtgt tcaaagaggg ggatccgatt     420
catctgcggt gtcactcctg gaagaatacc gccctgcata agtgacctac ctgcaaaac     480
ggcaagggcc gcaagtattt ccaccacaac tccgacttct atattcccaa agcgacgctg     540
aaggacagcg gcagctattt ctgccgtggg ctggtgggca gcaaaaatgt gagcagcgag     600
accgtgaata ttaccattac ccaagggggc catcatcatc atcatcat                  648
```

```
<210> SEQ ID NO 35
<211> LENGTH: 30
<212> TYPE: DNA
<213> ORGANISM: Artificial sequence
<220> FEATURE:
<223> OTHER INFORMATION: Oligonucleotide

<400> SEQUENCE: 35
gaatatcgtt gccagaccag cctgagcacc                                    30

<210> SEQ ID NO 36
<211> LENGTH: 30
<212> TYPE: DNA
<213> ORGANISM: Artificial sequence
<220> FEATURE:
<223> OTHER INFORMATION: Oligonucleotide

<400> SEQUENCE: 36
gatcgctcag ggtgctcagg ctggtctggc                                    30

<210> SEQ ID NO 37
<211> LENGTH: 216
<212> TYPE: PRT
<213> ORGANISM: Artificial sequence
<220> FEATURE:
<223> OTHER INFORMATION: FcR5a

<400> SEQUENCE: 37
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Phe Leu Glu Pro
            35                  40                  45

Gln Trp Asn Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His
    210                 215

<210> SEQ ID NO 38
<211> LENGTH: 648
<212> TYPE: DNA
<213> ORGANISM: Artificial sequence
<220> FEATURE:
<223> OTHER INFORMATION: FcR5a

<400> SEQUENCE: 38

```
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgtttctgga accgcagtgg aatcgcgtgc tggagaaaga ttctgtgacc     180
cttaaatgcc agggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggtgt tcaaagaggg ggatccgatt     420
catctgcggt gtcactcctg gaagaatacc gccctgcata agtgacccta cctgcaaaac     480
ggcaagggcc gcaagtattt ccaccacaac tccgacttct atattcccaa agcgacgctg     540
aaggacagcg gcagctattt ctgccgtggg ctggtgggca gcaaaaatgt gagcagcgag     600
accgtgaata ttaccattac ccaagggggc catcatcatc atcatcat              648
```

<210> SEQ ID NO 39
<211> LENGTH: 30
<212> TYPE: DNA
<213> ORGANISM: Artificial sequence
<220> FEATURE:
<223> OTHER INFORMATION: Oligonucleotide

<400> SEQUENCE: 39

```
cagggcgcgt atagcccgga tgataacagc                                       30
```

<210> SEQ ID NO 40
<211> LENGTH: 30
<212> TYPE: DNA
<213> ORGANISM: Artificial sequence
<220> FEATURE:
<223> OTHER INFORMATION: Oligonucleotide

<400> SEQUENCE: 40

```
cactgggtgc tgttatcatc cgggctatac                                       30
```

<210> SEQ ID NO 41
<211> LENGTH: 216
<212> TYPE: PRT
<213> ORGANISM: Artificial sequence
<220> FEATURE:
<223> OTHER INFORMATION: FcR5b

<400> SEQUENCE: 41

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Ala Met
                 20                  25                  30

Gly Met Arg Thr Glu Asp Leu Pro Lys Ala Glu Val Phe Leu Glu Pro
             35                  40                  45

Gln Trp Asn Arg Val Leu Glu Lys Asp Ser Val Thr Leu Lys Cys Gln
         50                  55                  60

Gly Ala Tyr Ser Pro Asp Asp Asn Ser Thr Gln Trp Phe His Asn Glu
 65                  70                  75                  80
```

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 42
<211> LENGTH: 648
<212> TYPE: DNA
<213> ORGANISM: Artificial sequence
<220> FEATURE:
<223> OTHER INFORMATION: FcR5b

<400> SEQUENCE: 42
atgaaaataa aaacaggtgc acgcatcctc gcattatccg cattaacgac gatgatgttt        60
tccgcctcgg ctctcgccaa aatcgaagaa gccatgggca tgcgtaccga agatctgccg       120
aaagcggagg tgtttctgga accgcagtgg aatcgcgtgc tggagaaaga ttctgtgacc       180
cttaaatgcc agggcgcgta tagcccggat gataacagca cccagtggtt ccacaatgaa       240
agcctgattt ccagccaggc gagcagctac cttattgatg cggcgacggt ggatgatagc       300
ggcgaatatc gttgccagac caacctgagc accctgagcg atccggtgca gctggaggtg       360
cacatcgggt ggcttctgtt acaggctcca cggtgggtgt tcaaagaggg ggatccgatt       420
catctgcggt gtcactcctg gaagaatacc gccctgcata agtgaccta cctgcaaaac        480 ggcaagggcc gcaagtattt ccaccacaac tccgacttct atattcccaa agcgacgctg       540
aaggacagcg gcagctattt ctgccgtggg ctggtgggca gcaaaaatgt gagcagcgag       600
accgtgaata ttaccattac ccaagggggc catcatcatc atcatcat                   648

<210> SEQ ID NO 43
<211> LENGTH: 216
<212> TYPE: PRT
<213> ORGANISM: Artificial sequence
<220> FEATURE:
<223> OTHER INFORMATION: FcR6a

<400> SEQUENCE: 43

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
 50                  55                  60

Gly Ala Tyr Ser Pro Asp Asp Asn Ser Thr Gln Trp Phe His Asn Glu
 65                  70                  75                  80

Ser Leu Ile Ser Ser Gln Ala Ser Ser Tyr Leu Ile Asp Ala Ala Thr
                 85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
            115                 120                 125

Ala Pro Arg Trp Val Phe Lys Glu Gly Asp Pro Ile His Leu Arg Cys
130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
            195                 200                 205

Gly Gly His His His His His His
            210                 215

<210> SEQ ID NO 44
<211> LENGTH: 648
<212> TYPE: DNA
<213> ORGANISM: Artificial sequence
<220> FEATURE:
<223> OTHER INFORMATION: FcR6a

<400> SEQUENCE: 44
atgaaaataa aaacaggtgc acgcatcctc gcattatccg cattaacgac gatgatgttt      60
tccgcctcgg ctctcgccaa atcgaagaa gccatgggca tgcgtaccga agatctgccg      120
aaagcggagg tgtttctgga accgcagtgg aatcgcgtgc tggagaaaga ttctgtgacc      180
cttaaatgcc agggcgcgta tagcccggat gataacagca cccagtggtt ccacaatgaa      240
agcctgattt ccagccaggc gagcagctac cttattgatg cggcgaccgt ggatgatagc      300
ggcgaatatc gttgccagac cagcctgagc accctgagcg atccggtgca gctggaggtg      360
cacatcgggt ggcttctgtt acaggctcca cggtgggtgt tcaaagaggg ggatccgatt      420
catctgcggt gtcactcctg gaagaatacc gccctgcata agtgacctac ctgcaaaac      480 ggcaagggcc gcaagtattt ccaccacaac tccgacttct atattcccaa agcgacgctg      540
aaggacagcg gcagctattt ctgccgtggg ctggtgggca gcaaaaatgt gagcagcgag      600
accgtgaata ttaccattac ccaagggggc catcatcatc atcatcat                   648

<210> SEQ ID NO 45
<211> LENGTH: 30
<212> TYPE: DNA
<213> ORGANISM: Artificial sequence
<220> FEATURE:
<223> OTHER INFORMATION: Oligonucleotide

<400> SEQUENCE: 45
gtgttcaaag tgggggatcc gattcatctg                                       30

<210> SEQ ID NO 46
<211> LENGTH: 30
<212> TYPE: DNA
<213> ORGANISM: Artificial sequence
<220> FEATURE:
<223> OTHER INFORMATION: Oligonucleotide

<400> SEQUENCE: 46
aatcggatcc cccactttga acacccaccg                               30

<210> SEQ ID NO 47
<211> LENGTH: 216
<212> TYPE: PRT
<213> ORGANISM: Artificial sequence
<220> FEATURE:
<223> OTHER INFORMATION: FcR6b

<400> SEQUENCE: 47

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Val Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 48
<211> LENGTH: 648
<212> TYPE: DNA
<213> ORGANISM: Artificial sequence
<220> FEATURE:
<223> OTHER INFORMATION: FcR6b

<400> SEQUENCE: 48
atgaaaataa aaacaggtgc acgcatcctc gcattatccg cattaacgac gatgatgttt     60
tccgcctcgg ctctcgccaa aatcgaagaa gccatgggca tgcgtaccga agatctgccg    120

```
aaagcggagg tgtttctgga accgcagtgg aatcgcgtgc tggagaaaga ttctgtgacc    180
cttaaatgcc agggcgcgta tagcccggat gataacagca cccagtggtt ccacaatgaa    240
agcctgattt ccagccaggc gagcagctac cttattgatg cggcgacggt ggatgatagc    300
ggcgaatatc gttgccagac caacctgagc accctgagcg atccggtgca gctggaggtg    360
cacatcgggt ggcttctgtt acaggctcca cggtgggtgt tcaaagtggg ggatccgatt    420
catctgcggt gtcactcctg gaagaatacc gccctgcata agtgacctaa cctgcaaaac    480
ggcaagggcc gcaagtattt ccaccacaac tccgacttct atattcccaa agcgacgctg    540
aaggacagcg gcagctattt ctgccgtggg ctggtgggca gcaaaaatgt gagcagcgag    600
accgtgaata ttaccattac ccaagggggc catcatcatc atcatcat                648
```

<210> SEQ ID NO 49
<211> LENGTH: 216
<212> TYPE: PRT
<213> ORGANISM: Artificial sequence
<220> FEATURE:
<223> OTHER INFORMATION: FcR7

<400> SEQUENCE: 49

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Asp Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Val Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215
```

<210> SEQ ID NO 50
<211> LENGTH: 648
<212> TYPE: DNA
<213> ORGANISM: Artificial sequence
<220> FEATURE:
<223> OTHER INFORMATION: FcR7

```
<400> SEQUENCE: 50
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgtttctgga accgcagtgg aatcgcgtgc tggagaaaga ttctgtgacc     180
cttaaatgcc agggcgcgta tagcccggat gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggtgt tcaaagtggg ggatccgatt     420
catctgcggt gtcactcctg aagaatacc gccctgcata aagtgaccta cctgcaaaac     480
ggcaagggcc gcaagtattt ccaccacaac tccgacttct atattcccaa agcgacgctg     540
aaggacagcg gcagctattt ctgccgtggg ctggtggca gcaaaaatgt gagcagcgag     600
accgtgaata ttaccattac ccaaggggc catcatcatc atcatcat                   648

<210> SEQ ID NO 51
<211> LENGTH: 30
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (13)..(14)
<223> OTHER INFORMATION: n stands for any base

<400> SEQUENCE: 51
ctgccgaaag cgnnkgtgtt tctggaaccg                                       30

<210> SEQ ID NO 52
<211> LENGTH: 30
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (14)..(15)
<223> OTHER INFORMATION: n stands for any base

<400> SEQUENCE: 52
ttccagaaac acmnncgctt tcggcagatc                                       30

<210> SEQ ID NO 53
<211> LENGTH: 30
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (12)..(13)
<223> OTHER INFORMATION: n stands for any base

<400> SEQUENCE: 53
aaccgcagtg gnnkcgcgtg ctggagaaag                                       30

<210> SEQ ID NO 54
<211> LENGTH: 30
<212> TYPE: DNA
<213> ORGANISM: Artificial sequence
<220> FEATURE:
<223> OTHER INFORMATION: Oligonucleotide
```

```
<220> FEATURE:
<221> NAME/KEY: misc_feature
<222> LOCATION: (10)..(11)
<223> OTHER INFORMATION: n stands for any base

<400> SEQUENCE: 54
agcacgcgmn nccactgcgg ttccagaaac                                         30

<210> SEQ ID NO 55
<211> LENGTH: 30
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (13)..(14)
<223> OTHER INFORMATION: n stands for any base

<400> SEQUENCE: 55
gtgttcaaag agnnkgatcc gattcatctg                                         30

<210> SEQ ID NO 56
<211> LENGTH: 30
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (11)..(12)
<223> OTHER INFORMATION: n stands for any base

<400> SEQUENCE: 56
aatcggatcm nnctctttga cacccaccg                                          30
```

FC-BINDING PROTEIN, METHOD FOR PRODUCING SAID PROTEIN, AND ANTIBODY ADSORBENT USING SAID PROTEIN, AND METHODS FOR PURIFYING AND IDENTIFYING ANTIBODY USING SAID ADSORBENT

TECHNICAL FIELD

The present invention relates to an Fc-binding protein that has affinity for immunoglobulins, to an antibody adsorbent using the protein, and to a method for purifying and identifying antibodies using the adsorbent. Specifically, the invention relates to an Fc-binding protein having higher stability against heat and acids compared to the wild type, to a method for producing the protein, and to an antibody adsorbent obtained by immobilizing the protein on an insoluble support. In particular, the invention relates to an adsorbent that can specifically adsorb antibodies that are antibodies with sugar chains, as well as to a method for purifying an antibody with sugar chains and to a method for identifying the presence or absence of sugar chain addition on antibodies, using the adsorbent.

BACKGROUND ART

Fc receptors are a group of molecules that bind to the Fc regions of immunoglobulin molecules. The individual molecules recognize single immunoglobulin isotypes, or those of the same group, by recognition domains on the Fc receptor, depending on the recognition domain belonging to an immunoglobulin superfamily. This determines which accessory cells will be driven in an immune response. Fc receptors can be further classified into several subtypes, namely Fcγ receptors which are receptors for IgG (immunoglobulin G), Fcε receptors that bind to the Fc region of IgE, and Fcα receptors that bind to the Fc region of IgA. Each of these receptors have still more detailed classifications, with reported Fcγ receptors including FcγRI, FcγRIIa, FcγRIIb, FcγRIIIa and FcγRIIIb (NPL 1: Takai. T., Jpn. J. Clin. Immunol., 28, 318-326, 2005).

Among the Fcγ receptors, FcγRIIIa are found on the cell surfaces of natural killer cells (NK cells) and macrophages, and they are important receptors involved in the activation of the important human immunomechanism ADCC (antibody-dependent cell-mediated cytotoxicity). The affinity between FcγRIIIa and human IgG has a coupling constant (KA), representing the binding strength, of $10^7$ M or less (NPL 2: J. Galori et al., Eur. J. Immunol., 27, 1928-1932, 1997). The amino acid sequence of human FcγRIIIa (SEQ ID NO: 1) has been published in public databases such as UniProt (Accession number: P08637). Moreover, the functional domain on the structure of human FcγRIIIa, the signal peptide sequence for spanning of the cell membrane, and the position of the transmembrane region have likewise been published. FIG. 1 shows a structural diagram of human FcγRIIIa. The amino acid numbers in FIG. 1 correspond to the amino acid numbers in SEQ ID NO: 1. Specifically, the region from methionine (Met) at position 1 to alanine (Ala) at position 16 of SEQ ID NO: 1 is the signal sequence (S), the region from glycine (Gly) at position 17 to glutamine (Gln) at position 208 is the extracellular domain (EC), the region from valine (Val) at position 209 to valine (Val) at position 229 is the transmembrane region (TM), and the region from lysine (Lys) at position 230 to lysine (Lys) at position 254 is the cytoplasmic (C). It is known that FcγRIIIa binds particularly strongly to IgG1 and IgG3, among the human IgG subclasses from IgG1 to IgG4, while binding weakly to IgG2 and IgG4.

The development of drugs utilizing the specificity of monoclonal antibodies (antibody drugs) has been progressing in recent years. Among the human IgG used in antibody drugs, it is known that ADCC (antibody-dependent cell-mediated cytotoxicity) activity varies due to differences in N-linked sugar chains added to the asparagine residue at position 297 of the Fc region, and it has been reported that ADCC activity is particularly increased with antibodies from which fucose sugar chains have been removed (NPL 3: Shinkawa, T., J. Biol. Chem., 278, 3466-3473, 2003). In other words, the sugar chain structure of an antibody is highly significant for an antibody drug. However, antibody drugs are usually produced using gene recombinant technology with animal cells as the host, and it is difficult to control the sugar chains that are added to antibodies inside the host. Furthermore, much time and effort is required to analyze the sugar chains of produced antibodies.

CITATION LIST

Non-Patent Literature

NPL 1: Takai, T., Jpn. J. Clin. Immonol., 28, 318-326, 2005
NPL 2: J. Galon et al., Eur. J. Immonol., 27, 1928-1932, 1997
NPL 3: Shinkawa, T., J. Biol. Chem., 278, 3466-3473, 2003

SUMMARY OF INVENTION

Technical Problem

The first object of the invention is directed to providing an Fc-binding protein with increased stability particularly against heat and acids, a method for producing the protein, and an antibody adsorbent using the protein. The second object of the invention is directed to providing a method that allows identification of the presence or absence of sugar chain addition to an antibody, and a material to be used in the method.

Solution to Problem

As a result of diligent research for achieving the first object, the present inventors have identified an amino acid residue involved in increased stability of human FcγRIIIa, and have found that variants in which said amino acid residue has been substituted with other amino acid residues have excellent stability against heat and acids, thereby have completed this invention.

As a result of diligent research for achieving the second object, the present inventors have found that it is possible to identify the presence or absence of sugar chain addition on antibodies by using an adsorbent obtained by immobilizing FcγRIIIa, which is a receptor for IgG (Fcγ receptor), on an insoluble support, thereby have further completed this invention.

That is, the present application encompasses the following aspects (A) to (Z):

(A) An Fc-binding protein comprising the amino acid residues from position 17 to position 192 of the amino acid sequence of SEQ ID NO: 1, wherein at least one amino acid substitution selected from the following (1) to (40) is occurred among the amino acid residues from position 17 to position 192:

(1) A substitution of arginine for methionine at position 18 of SEQ ID NO: 1.
(2) A substitution of glutamic acid for valine at position 27 of SEQ ID NO: 1.
(3) A substitution of leucine or serine for phenylalanine at position 29 of SEQ ID NO: 1.
(4) A substitution of glutamine for leucine at position 30 of SEQ ID NO: 1.
(5) A substitution of aspartic acid, glycine, lysine, leucine, asparagine, proline, serine, threonine or histidine for tyrosine at position 35 of SEQ ID NO: 1.
(6) A substitution of isoleucine or threonine for lysine at position 46 of SEQ ID NO: 1.
(7) A substitution of histidine or leucine for glutamine at position 48 of SEQ ID NO: 1.
(8) A substitution of histidine for alanine at position 50 of SEQ ID NO: 1.
(9) A substitution of aspartic acid or histidine for tyrosine at position 51 of SEQ ID NO: 1.
(10) A substitution of aspartic acid or glycine for glutamic acid at position 54 of SEQ ID NO: 1.
(11) A substitution of threonine for asparagine at position 56 of SEQ ID NO: 1.
(12) A substitution of arginine for glutamine at position 59 of SEQ ID NO: 1.
(13) A substitution of tyrosine for phenylalanine at position 61 of SEQ ID NO: 1.
(14) A substitution of aspartic acid for glutamic acid at position 64 of SEQ ID NO: 1.
(15) A substitution of arginine for serine at position 65 of SEQ ID NO: 1.
(16) A substitution of aspartic acid for alanine at position 71 of SEQ ID NO: 1.
(17) A substitution of leucine, serine or tyrosine for phenylalanine at position 75 of SEQ ID NO: 1.
(18) A substitution of asparagine for aspartic acid at position 77 of SEQ ID NO: 1.
(19) A substitution of serine for alanine at position 78 of SEQ ID NO: 1.
(20) A substitution of glutamic acid or valine for aspartic acid at position 82 of SEQ ID NO: 1.
(21) A substitution of arginine for glutamine at position 90 of SEQ ID NO: 1.
(22) A substitution of serine for asparagine at position 92 of SEQ ID NO: 1.
(23) A substitution of arginine or methionine for leucine at position 93 of SEQ ID NO: 1.
(24) A substitution of alanine or serine for threonine at position 95 of SEQ ID NO: 1.
(25) A substitution of glutamine for leucine at position 110 of SEQ ID NO: 1.
(26) A substitution of glutamine for arginine at position 115 of SEQ ID NO: 1.
(27) A substitution of leucine for tryptophan at position 116 of SEQ ID NO: 1.
(28) A substitution of tyrosine for phenylalanine at position 118 of SEQ ID NO: 1.
(29) A substitution of glutamic acid for lysine at position 119 of SEQ ID NO: 1.
(30) A substitution of valine for glutamic acid at position 120 of SEQ ID NO: 1.
(31) A substitution of aspartic acid or glycine for glutamic acid at position 121 of SEQ ID NO: 1.
(32) A substitution of serine or tyrosine for phenylalanine at position 151 of SEQ ID NO: 1.
(33) A substitution of threonine for serine at position 155 of SEQ ID NO: 1.
(34) A substitution of serine for threonine at position 163 of SEQ ID NO: 1.
(35) A substitution of glycine for serine at position 167 of SEQ ID NO: 1.
(36) A substitution of glycine for serine at position 169 of SEQ ID NO: 1.
(37) A substitution of tyrosine for phenylalanine at position 171 of SEQ ID NO: 1.
(38) A substitution of lysine, serine or isoleucine for asparagine at position. 180 of SEQ ID NO: 1.
(39) A substitution of serine for threonine at position 185 of SEQ ID NO: 1.
(40) A substitution of lysine for glutamine at position 192 of SEQ ID NO: 1

(B) The Fc-binding protein according to (A), comprising the amino acid residues from position 17 to position 192 of the amino acid sequence of SEQ ID NO: 1, wherein at least tyrosine at position 35 of SEQ ID NO: 1 is substituted with aspartic acid, glycine, lysine, leucine, asparagine, proline, serine, threonine or histidine, among the amino acid residues from position 17 to position 192.

(C) The Fc-binding protein according to (B), comprising the amino acid residues from position 17 to position 192 of the amino acid sequence of SEQ ID NO: 1, wherein at least tyrosine at position 35 of SEQ ID NO: 1 is substituted with asparagine or proline, among the amino acid residues from position 17 to position 192.

(D) The Fc-binding protein according to (C), comprising the amino acid residues from position 33 to position 208 of the amino acid sequence of any one selected from SEQ ID NO: 27, SEQ ID NO: 31, SEQ ID NO: 33, SEQ ID NO: 37, SEQ ID NO: 41, SEQ ID NO: 43, SEQ ID NO: 47 and SEQ ID NO: 49.

(E) The Fc-binding protein according to (D), consisting of the amino acid sequence of any one selected from SEQ ID NO: 27, SEQ ID NO: 31, SEQ ID NO: 33, SEQ ID NO: 37, SEQ ID NO: 41, SEQ ID NO: 43, SEQ ID NO: 47 and SEQ ID NO: 49.

(F) The Fc-binding protein according to any one of to (C), wherein at least one amino acid substitution selected from the following (41) to (44) is occurred:
(41) A substitution of histidine or arginine for leucine at position 66 of SEQ ID NO: 1.
(42) A substitution of aspartic acid for glycine at position 147 of SEQ ID NO: 1
(43) A substitution of histidine for tyrosine at position 158 of SEQ ID NO: 1.
(44) A substitution of phenylalanine for valine at position 176 of SEC) ID NO: 1.

(G) An adsorbent obtained by immobilizing the Fc-binding protein according to any one of (A) to (F) on an insoluble support.

(H) A method for purifying an antibody using the adsorbent according to (G).

(I) A method for identifying differences in sugar chain structures of antibodies, by separating the antibodies using the adsorbent according to (G).

(J) An antibody obtained by the method according to (H).

(K) A method for separating a sugar chain using the adsorbent according to (G).

(L) A sugar chain obtained by the method according to (K).

(M) A polynucleotide coding for the Fc-binding protein according to any one of (A) to (F).

(N) An expression vector comprising the polynucleotide according to (M).

(O) A transformant obtained by transforming a host with the expression vector according to (N).

(P) A transformant according to (O), wherein the host is *E. coli*.

(Q) A method for producing an Fc-binding protein, wherein the Fc-binding protein is expressed by culturing the transformant according to (O) or (P), and the expressed Fc-binding protein is recovered from the cultured product.

(R) An adsorbent for an antibody with a sugar chain, obtained by immobilizing human FcγRIIIa on an insoluble support.

(S) The adsorbent according to (R), wherein the human FcγRIIIa is a polypeptide comprising at least amino acid residues from glycine at position 17 to glutamine at position 192 of the amino acid sequence of SEQ ID NO: 1.

(I) The adsorbent according to (R), wherein the human FcγRIIIa is a polypeptide comprising at least the amino acid residues from glycine at position 17 to glutamine at position 192 of the amino acid sequence of SEQ ID NO: 1, and having a substitution, insertion or deletion of at least one other amino acid residue among those amino acid residues.

(1j) The adsorbent according to (T), wherein the human FcγRIIIa is a polypeptide comprising at least the amino acid residues from glycine at position 17 to glutamine at position 192 of the amino acid sequence of SEQ ID NO: 1, and having at least any one amino acid substitution selected from following (i) to (iv), of the amino acid residues from position 17 to position 192:

(i) A substitution of histidine or arginine for leucine at position 66 of SEQ ID NO: 1.

(ii) A substitution of aspartic acid for glycine at position 147 of SEQ ID NO: 1.

(iii) A substitution of histidine for tyrosine at position 158 of SEQ ID NO: 1.

(iv) A substitution of phenylalanine for valine at position 176 of SEQ ID NO: 1.

(V) A method for purifying an antibody with a sugar chain, the method comprising a step of adding a solution containing an antibody with a sugar chain to the adsorbent according to any one of (R) to (U) to adsorb it onto the adsorbent, and a step of eluting the antibody with a sugar chain adsorbed onto the adsorbent using an eluent.

(W) An antibody obtained by the method according to (V).

(X) A method for identifying the presence or absence of sugar chain addition to an antibody, using the adsorbent according to any one of (R) to (U).

(Y) A method for separating sugar chains using the adsorbent according to any one of (R) to (U).

(Z) A sugar chain obtained by the method according to (Y).

The present invention will now be explained in greater detail.

The Fc-binding protein of the invention is a protein having affinity for the Fc region of an antibody and comprising at least the amino acid residues from glycine at position 17 to glutamine at position 192 among the extracellular domain of human FcγRIIIa consisting of the amino acid sequence of SEQ ID NO: 1 (region EC in FIG. 1), wherein an amino acid substitution is occurred at a specific position among the amino acid residues from position 17 to position 192. Thus, the Fc-binding protein of the invention may include all or a portion of the signal peptide region (S in FIG. 1) at the N-terminal end of the extracellular domain, or may include all or a portion of the transmembrane region (TM in FIG. 1) and the extracellular domain (C in FIG. 1) at the C-terminal end of the extracellular domain. The amino acid substitution at the specific position is, specifically, at least one substitution selected from Met18Arg (this designation indicating that the methionine at position 18 of SEQ ID NO: 1 is substituted with arginine, the same hereunder), Val27Glu, Phe29Leu, Phe29Ser, Leu30Gln, Tyr35Asp, Tyr35Gly, Tyr35Lys, Tyr35Leu, Tyr35Asn, Tyr35Pro, Tyr35Ser, Tyr35Thr, Tyr35His, Lys46Ile, Lys46Thr, Gln48His, Gln48Leu, Ala50His, Tyr51Asp, Tyr51His, Glu54Asp, Glu54Gly, Asn56Thr, Gln59Arg, Phe61Tyr, Glu64Asp, Ser65Arg, Ala71Asp, Phe75Leu, Phe75Ser, Phe75Tyr, Asp77Asn, Ala78Ser, Asp82Glu, Asp82Val, Gln90Arg, Asn92Ser, Leu93Arg, Leu93Met, Thr95Ala, Thr95Ser, Leu110Gln, Arg115Gln, Trp116Leu, Phe118Tyr, Lys119Glu, Glu120Val, Glu121Asp, Glu121Gly, Phe151Ser, Phe151Tyr, Ser155Thr, Thr163Ser, Ser167Gly, Ser169Gly, Phe171Tyr, Asn180Lys, Asn180Ser, Asn180Ile, Thr185Ser and Gln192Lys, in the amino acid sequence of SEQ ID NO: 1. Among them, any substitutions selected from Tyr35Asp, Tyr35Gly, Tyr35Lys, Tyr35Leu, Tyr35Asn, Tyr35Pro, Tyr35Ser, Tyr35Thr, Tyr35His and Glu121Gly are preferred, because they increase thermal stability. Moreover, wild type human FcγRIIIa is known to include variants having the substitutions Leu66His, Leu66Arg, Gly147As, Tyr158His and Val176Phe, and therefore these amino acid substitutions may also be included, in addition to the amino acid substitutions at the specific positions listed above.

When the Fc-binding protein of the invention is to be produced by amino acid substitution, amino acid residues at the specific positions may be substituted with amino acids other than the amino acids mentioned above, as long as they have antibody binding activity. As one example, there may be mentioned conservative substitutions which are substitutions between amino acids in which either or both the physical and chemical properties of both amino acids are similar. It is known to those skilled in the art that a conservative substitution makes protein. function maintained between proteins with the substitution and proteins without the substitution, as a general rule which is not limited to Fc-binding protein. Examples of conservative substitutions include substitutions between glycine and alanine, aspartic acid and glutamic acid, serine and praline or glutamic acid and alanine (Structure and Function of Protein, Medical Science International, Inc., 9, 2005).

For the Fc-binding protein of the invention, there are no particular restrictions on the number of amino acids that aresubstituted. As an example, it includes the Fc-binding proteins according to following (a) to (h). These Fc-binding proteins are preferred from the viewpoint of increasing stability against heat and acid. (a) An Fc-binding protein comprising the amino acid residues from position 17 to position 192 of the amino acid sequence of SEQ ID NO: 1, wherein the amino acid substitutions Val27Glu and. Tyr35Asn are occurred in the amino acid residues from position 17 to position 192 (an Fc-binding protein comprising the amino acid sequence from position 33 to position 208 of the amino acid sequence of SEQ ID NO: 27), (b) an Fc-binding protein comprising the amino acid residues from position 17 to position 192 of the amino acid sequence of SEQ ID NO: 1, wherein the amino acid substitutions Val27Glu, Tyr35Asn and Phe75Leu are occurred in the amino acid residues from position 17 to position 192 (an Fc-binding protein comprising the amino acid sequence from position 33 to position 208 of the amino acid sequence of SEQ ID NO: 31), (c) an Fc-binding protein comprising the amino acid residues from position 17 to position 192 of the amino acid sequence of SEQ ID NO: 1, wherein the amino acid substitutions Val27Glu, Tyr35Asn, Phe75Leu and Glu121Gly are occurred in the amino acid residues from position 17 to position 192 (an Fc-binding protein comprising the amino acid sequence from position 33 to position 208 of the amino acid sequence of SEQ. ID NO: 33), (d) an Fc-binding protein comprising the amino acid residues from position 17 to position 192 of the amino acid sequence of SEQ ID NO: 1, wherein the amino acid substitutions Val27Glu, Tyr35Asn, Phe75Leu, Asn92Ser and Glu121Gly are occured in the amino acid residues from position 17 to position 192 (an Fc-binding protein comprising the amino acid sequence from position 33 to position 208 of the amino acid sequence of SEQ ID NO: 37), (e) an Fc-binding protein comprising the amino acid residues from position 17 to position 192 of the amino acid sequence of SEQ ID NO: 1, wherein the amino acid substitutions Val27Glu, Tyr35Asn, Glu54Asp, Phe75Leu and Glu121Gly are occured in the amino acid residues from position 17 to position 192 (an Fc-binding protein comprising the amino acid sequence from position 33 to position 208 of the amino acid sequence of SEQ ID NO: 41), (f) an Fc-binding protein comprising the amino acid residues from position 17 to position 192 of the amino acid sequence of SEQ ID NO: 1, wherein the amino acid substitutions Val27Glu, Tyr35Asn, Glu54Asp, Phe75Leu, Asn92Ser and Glu121Gly are occured in the amino acid residues from position 17 to position 192 (an Fc-binding protein comprising the amino acid sequence from position 33 to position 208 of the amino acid sequence of SEQ ID NO: 43), (g) an Fc-binding protein comprising the amino acid residues from position 17 to position 192 of the amino acid sequence of SEQ ID NO: 1, wherein the amino acid substitutions Val27Glu, Tyr35Asn, Glu54Asp, Phe75Leu, Glu120Val and Glu121Gly are occured in the amino acid residues from position 17 to position 192 (an Fc-binding protein comprising the amino acid sequence from position 33 to position 208 of the amino acid sequence of SEQ ID NO: 47), and (h) an Fc-binding protein comprising the amino acid residues from position 17 to position 192 of the amino acid sequence of SEQ ID NO: 1, wherein the amino acid substitutions Val27Glu, Tyr35Asn, Glu54Asp, Phe75Leu, Asn92Ser, Glu120Val and Glu121Gly are occured in the amino acid residues from position 17 to position 192 (an Fc-binding protein comprising the amino acid sequence from position 33 to position 208 of the amino acid sequence of SEQ ID NO: 49).

The amino acid sequence of human FcγRIIIa (SEQ ID NO: 1) used as the ligand for the adsorbent of the invention has been published in public databases such as UniProt (Accession number: P08637). Moreover, the functional domain, the signal peptide sequence for transmembrane, and the position of the transmembrane region on the structure of human FcγRIIIa have likewise been published. FIG. 1 shows a structural diagram of human FcγRIIIa. The amino acid numbers in FIG. 1 correspond to the amino acid numbers in SEQ III) NO: 1. Specifically, the region from methionine (Met) at position 1 to alanine (Ala) at position 16 of SEQ ID NO: 1 is the signal sequence (S), the region from glycine (Gly) at position 17 to glutamine (Gln) at position 208 is the extracellular domain (EC), the region from valine (Val) at position 209 to valine (Val) at position 229 transmembrane region (TM), and the region from lysine (Lys) at position 230 to lysine (Lys) at position 254 is the cytoplasmic (C). The human FcγRIIIa used as the ligand for the adsorbent of the invention does not necessarily have to employ the full-length human FcγRIIIa (SEQ ID NO: 1), and need only be a polypeptide including at least the amino acid residues from glycine at position 17 to glutamine at position 192 of the amino acid sequence of SEQ ID NO: 1. Also encompassed in human FcγRIIIa to be used as a ligand for the adsorbent of the invention are polypeptides including at least the amino acid residues from glycine at position 17 to glutamine at position 192 of the amino acid sequence of SEQ ID NO: 1, wherein a substitution, insertion or deletion of at least one other amino acid residue among those amino acid residues. Naturally-occurring human FcγRIIIa variants are known to have histidine (His) or arginine (Arg) substituting for leucine (Leu) at position 66, aspartic acid (Asp) substituting for glycine (Gly) at position 147, histidine (His) substituting for tyrosine (Tyr) at position 158 or phenylalanine (Phe) substituting for valine (Val) at position 176, and therefore polypeptides having at least one of these amino acid substitutions are also encompassed in the human FcγRIIIa to be used as the ligand for the adsorbent of the invention.

The Fc-binding protein, or the human FcγRIIIa as the ligand for the adsorbent, according to the invention, may also have added to the N-terminal end or the C-terminal end, an oligopeptide useful for separation from solution in the presence of contaminants. Such oligopeptides include polyhistidine, polylysine, polyarginine, polyglutamic acid and polyaspartic acid. Moreover, it may further have, added to the N-terminal end or C-terminal end of the Fc-binding protein or the human FcγRIIIa as the ligand of the adsorbent, according to the invention, an oligopeptide including cysteine, which is useful for immobilizing the Fc-binding protein or the human FcγRIIIa as the ligand of the adsorbent, according to the invention, to a solid phase such as a support for chromatography. The length of the oligopeptide to be added to the N-terminal end or C-terminal end of the Fc-binding protein or the human FcγRIIIa as the ligand of the adsorbent is not particularly restricted so long as the IgG affinity or stability of the Fc-binding protein or the human. FcγRIIIa as the ligand of the adsorbent, according to the invention, is not impaired. When the oligopeptide is added to the Fc-binding protein or the human FcγRIIIa as the ligand of the adsorbent, according to the invention, first a polynucleotide coding for the oligopeptide may be prepared and then added by genetic engineering according to a method known to those skilled in the art so that the oligopeptide is added to the N-terminal end or C-terminal end of the Fc-binding protein or human FcγRIIIa, or the chemically synthesized oligopeptide may be chemically bonded to the N-terminal end or C-terminal end of the Fc-binding protein or the human FcγRIIIa of the invention. In addition, a signal peptide that promotes efficient host expression may be added to the N-terminal end of the Fc-binding protein or the human FcγRIIIa as the ligand of the adsorbent, according to the invention. Examples for the signal peptide, when the host is *E. coli*, include signal peptides that secrete proteins in the periplasm, such as PelB, DsbA, MalE (the region from position 1 to position 26 of the amino acid sequence listed as UniProt No. P0AEX9) or TorT (Japanese Unexamined Patent Publication No. 2011-097898).

Examples of the methods for preparing the polynucleotide of the invention include (I) a method in which the amino acid sequence of the Fc-binding protein or the human FcγRIIIa as the ligand of the adsorbent is converted to a nucleotide sequence, and a polynucleotide including that nucleotide sequence is artificially synthesized, and (II) a method in which polynucleotides including the full or partial sequence for the Fc-binding protein or human FcγRIIIa are prepared directly in an artificial manner, or are prepared by a DNA amplification method such as PCR from cDNA for the Fc-binding protein or human FcγRIIIa, and the prepared polynucleotides are linked by an appropriate method. In the method of (I), during conversion from the amino acid sequence to the nucleotide sequence, the frequency of codon usage in the host to be transformed is preferably considered for the conversion. As an example, when the host is E. coli (Escherichia coli), the usage frequencies of AGA/AGG/CGG/CGA for arginine (Arg), ATA for isoleucine (Ile), CIA for leucine (Leu), GGA for glycine (Gly) and CCC for proline (Pro) are low (being rare codons), and therefore the conversion may be carried out in a manner that avoids these codons. Analysis of the codon usage frequencies may be accomplished utilizing a public database (for example, the Codon Usage Database found on the home page of the Kazusa DNA Research Institute).

An error-prone PCR method may be used for introduction of a mutation into a polynucleotide of the invention. The reaction conditions for the error-prone PCR method are not particularly restricted so long as they are conditions allowing introduction of the desired mutation into a polynucleotide coding for human FcγRI (or Fc-binding protein), and for example, a mutation may be introduced into the polynucleotide by PCR in which non-homogeneous concentrations of the four different deoxynucleotides (dATP/dTTP/dCTP/dGTP) as substrates are prepared, and $MnCl_2$ is added to the PCR reaction mixture at concentrations from 0.01 to 10 mM (preferably 0.1 to 1 mM). As methods of mutagenesis other than error-prone PCR, there may be mentioned methods in which a polynucleotide including the full or partial sequence of human FcγRI is contacted with and acted on by a chemical agent that acts as a mutagen, or is irradiated with ultraviolet rays, to introduce mutations into the polynucleotide. In such methods, the chemical agent used as the mutagen may be a mutagenic chemical agent that is commonly used by those skilled in the art, such as hydroxylamine, N-methyl-N'-nitro-N-nitrosoguanidine, nitrous acid, sulfurous acid or hydrazine.

When polynucleotide of the invention is used for transformation of a host, the polynucleotide of the invention itself may be used, but it is more preferred to use a polynucleotide of the invention having an expression vector (for example, bacteriophage, cosmids, plasmids or the like that are commonly used for transformation of prokaryotic cells or eukaryotic cells) inserted at an appropriate location. The expression vector is not particularly restricted so long as it is stably present and can replicate in the host to be transformed, and when E. coli is used as the host, examples include pET plasmid vector, pUC plasmid vector, pTrc plasmid vector, pCDF plasmid vector and pBBR plasmid vector. The "appropriate location" is a location where the replicating function of the expression vector, the desired antibiotic marker and the transfer-associated regions are not destroyed. When a polynucleotide of the invention is to be inserted in the expression vector, it is preferably inserted in a manner linked to a functional polynucleotide such as a promoter, that is necessary for expression. Examples of such promoters include, for E. coli as the host, tip promoter, tac promoter, trc promoter, lac promoter, T7 promoter, recA promoter and lpp promoter, as well as the λ phage λPL promoter and λPR promoter.

Transformation of the host using an expression vector in which the polynucleotide of the invention has been inserted (hereunder referred to as the "expression vector of the invention"), prepared in the manner described above, can be accomplished by a method commonly employed by those skilled in the art. For example, when selecting a microorganism belonging to the genus Escherichia (E. coli JM109, E. coli BL21(DE3), E. coli W3110 or the like) as the host, the transformation may be carried out by a method described in the known literature (for example, Molecular Cloning, Cold Spring Harbor Laboratory, 256, 1992). The transformants produced by transformation by such a method can be obtained by screening by an appropriate method to obtain transformants capable of expressing the Fc-binding protein of the invention (hereunder referred to as "transformants of the invention"). There are no particular restrictions on the host that is to express the Fc-binding protein or the human FcγRIIIa as the ligand of the adsorbent, according to the invention, and examples include animal cells (CHO cells, HEK cells, Hela cells, COS cells and the like), yeast (Saccharomyces cerevisiae, Pichia pastoris, Hansenula polymorpha, Schizosaccharomyces japonicus, Schizosaccharomyces octosporus, Schizosaccharomyces pombe and the like), insect cells (Sf9, Sf21 and the like), E. coli (JM109, BL21(DP3), W3110 and the like), and Bacillus subtilis. Animal cells and E. coli are generally preferred as the host from the standpoint of productivity, with E. coli being more preferred as the host.

In order to prepare an expression vector of the invention from transformants of the invention, it may be prepared from a cultured product obtained by culturing the transformants of the invention, using an alkaline extraction method or a commercially available extraction kit such as a QIAprep Spin Miniprep kit (product of Qiagen Inc.). By culturing the transformants of the invention and recovering the Fc-binding protein of the invention from the obtained cultured product, it is possible to produce Fc-binding protein according to the invention. Throughout the present specification, the term "cultured product" includes the cultured cells of the transformants of the invention themselves, as well as the culture medium used for culturing. The transformants used in the method for producing a protein according to the invention may be cultured in medium suitable for culturing of the host, and when the host is E. coli, LB (Luria-Bertani) culture medium, supplemented with necessary nutrients, may be mentioned as a preferred medium. In order to selectively grow the transformants of the invention based on whether the vector of the invention has been introduced, preferably a chemical agent for a drug resistance gene present in the vector is added to the medium and culturing is performed. For example, when the vector includes a kanamycin resistance gene, kanamycin may be added to the culture medium. There may also be added to the culture medium, in addition to carbon, nitrogen and inorganic salt sources, various appropriate nutrients, and optionally one or more different reducing agents selected from the group consisting of glutathione, cysteine, cystamine, thioglycolate and dithiothreitol. There may also be added reagents that promote protein secretion from the transformants into the medium, such as glycine, and specifically when the host is E. coli, glycine is preferably added at no greater than 2% (w/v) to the culture medium. When the host is E. coli, the culturing temperature will generally be 10° C. to 40° C., preferably 20° C. to 37° C. and more preferably around 25° C., although this may be selected depending on the properties of the protein to be expressed. The pH of the culture medium is from pH 6.8 to pH 7.4 and preferably around pH 7.0, when the host is E. coli. When an inducible promoter is included in the vector of the invention, it is preferably induced under conditions such that the Fc-binding protein of the invention can be satisfactorily expressed. The inducing agent may be IPTG (isopropyl-β-D-thiogalactopyranoside), for example. When the host is E. coli, the turbidity of the culture solution is measured (at an absorbance of 600 nm), a suitable amount of IPTG is added when the value reaches about 0.5 to 1.0, and then culturing is continued, thereby allowing expression of the Fc-binding protein to be induced. The concentration of the IPTG added may be appropriately selected in the range of 0.005 to 1.0 mM, and preferably in the range of 0.01 to 0.5 mM. The various conditions for IPTG induction may be known conditions in the technical field.

For recovery of the Fc-binding protein of the invention from the cultured product obtained by culturing the transformants of the invention, the Fc-binding protein of the invention may be recovered by isolation and purification from the cultured product by a method suited for the form of expression of the Fc-binding protein of the invention in the transformants of the invention. For example, in the case of expression in the culture supernatant, the cells may be isolated by centrifugal separation and the Fc-binding protein of the invention purified from the obtained culture supernatant. When the expression is intracellular (including the periplasm), the cells may be collected by centrifugal separation, and then an enzyme treatment agent, surfactant or the like added to disrupt the cells, after which the Fc-binding protein of the invention may be extracted and purified. A method known in the technical field may be used for purification of the Fc-binding protein of the invention, an example of which is isolation/purification using liquid chromatography. Liquid chromatography includes ion-exchange chromatography, hydrophobic interaction chromatography, gel filtration chromatography and affinity chromatography, and these chromatography methods may also be combined for purification to prepare a high-purity Fc-binding protein of the invention. The method of measuring the binding activity of the obtained Fc-binding protein of the invention for IgG may be, for example, measurement of the binding activity for IgG using an Enzyme-Linked ImmunoSorbent Assay (hereunder, ELISA), a surface plasmon resonance method, or similar. The IgG used for measurement of the binding activity is preferably human IgG, and most preferably human IgG1 or human IgG3.

An adsorbent of the invention can be produced by binding the Fc-binding protein or human FcγRIIIa according to the invention to an insoluble support. There are no particular restrictions on the insoluble support, and examples include supports where the starting material is a polysaccharide such as agarose, alginate, carrageenan, chitin, cellulose, dextrin, dextran or starch, supports where the starting material is an synthetic polymer such as polyvinyl alcohol polymethacrylate, poly(2-hydroxyethyl methacrylate) or polyurethane, and supports where the starting material is a ceramic such as silica. Preferred among these as the insoluble support are supports where the starting material is a polysaccharide and supports where the starting material is a synthetic polymer. Examples of preferred supports include hydroxyl-introduced polymethacrylate gels such as Toyopearl (by Tosoh Corp.), agarose gels such as Sepharose (by GE Healthcare), and cellulose gels such as CELLUFINE (by JNC). There are no particular restrictions on the form of the insoluble support, and it may be granular, non-granular, porous or non-porous.

For immobilization of the Fc-binding protein or human FcγRIIIa on the insoluble support, the insoluble support may be provided with active groups such as N-hydroxysuccinic acid imide (NHS) activated ester groups, epoxy, carboxyl, maleimide, haloacetyl, tresyl, formyl and haloacetamide groups, immobilization being accomplished by covalent bonding between the human Fc-binding protein and insoluble support through the active groups. The support with the active groups may be a commercially available support used as is, or it may be prepared by introducing active groups onto the support surface under appropriate reaction conditions. Examples of commercially available supports with active groups include TOYOPEARL AF-Epoxy-650M and TOYOPEARL AF-Tresyl-650M (both by Tosoh Corp.), HiTrap NHS-activated HP Columns, NHS-activated Sepharose 4 Fast Flow and Epoxy-activated Sepharose 6B (all by GE Healthcare), and SulfoLink Coupling Resin (by Thermo Scientific).

Examples of methods for introducing active groups onto the support surface, on the other hand, include methods in which one site of a compound with two or more active sites is reacted with hydroxyl, epoxy, carboxyl and amino groups present on the support surface. Compounds having epoxy groups introduced onto hydroxyl or amino groups on the support surface, as examples of such compounds, include epichlorhydrin, ethanediol diglycidyl ether, butanediol diglycidyl ether and hexanediol diglycidyl ether. Compounds that introduce carboxyl groups onto the support surface after epoxy groups have been introduced onto the support surface by the compound, include 2-mercaptoacetic acid, 3-mercaptopropionic acid, 4-mercaptobutyric acid, 6-mercaptobutyric acid, glycine, 3-aminopropionic acid, 4-aminobutyric acid and 6-aminohexanoic acid.

Examples of compounds that introduce maleimide groups onto hydroxyl or epoxy, carboxyl or amino groups present on the support surface include N-(ε-maleimidecaproic acid) hydrazide, N-(ε-maleimidepropionic acid)hydrazide, 4-[4-N-maleimidephenyl]acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimide)phenylisocyanato, 2-maleimideacetic acid, 3-maleimidepropionic acid, 4-maleimidebutyric acid, 6-maleimidehexanoic acid, (N-[α-maleimideacetoxy]succinimide ester), (m-maleimidebenzoyl) N-hydroxysuccinimide ester, (succinimidyl-4-[maleimidemethyl]cyclohexane-1-carbonyl-[6-aminohexanoic acid]), (succinimidyl-4-[maleimidemethyl] cyclohexane-1-carboxylic acid), (p-maleimidebenzoyl)N-hydroxysuccinimide ester and (m-maleimidebenzoyl)N-hydroxysuccinimide ester.

Examples of compounds that introduce haloacetyl groups onto hydroxyl or amino groups present on the support surface include chloroacetic acid, bromoacetic acid, iodoacetic acid, chloroacetic acid chloride, bromoacetic acid chloride, bromoacetic acid bromide, chloroacetic anhydride, bromoacetic anhydride, iodoacetic anhydride, 2-(iodoacetamide)acetic acid-N-hydroxysuccinimide ester, 3-(bromoacetamide)propionic acid-N-hydroxysuccinimide ester and 4-(iodoacetyl)aminobenzoic acid-N-hydroxysuccinimide ester. There may also be mentioned methods in which an ω-alkenylalkaneglycidyl ether is reacted with hydroxyl or amino groups present on the support surface, and then the ω-alkenyl site is halogenated with a halogenating agent and activated. Examples of ω-alkenylalkaneglycidyl ethers include allyl glycidyl ether, 3-butenyl glycidyl ether and 4-pentenyl glycidyl ether, and examples of halogenating agents include N-chlorosuccinimide, N-bromosuccinimide and N-iodosuccinimide.

A different example of a method for introducing active groups onto the support surface, is a method in which activated groups are introduced onto the carboxyl groups present on the support surface, using a condensation agent and an additive. Examples of condensation agents include 1-ethyl-3-(3-dimethylaminopropyl)carbodiimide (EDC), ddcyclohexylcarbodiimide and carbonyldiimidazole. Examples of additives include N-hydroxysuccinic acid imide (NHS), 4-nitrophenol and 1-hydroxybenzotriazole.

Examples for the buffering solution to be used during immobilization of the Fc-binding protein or human FcγRIIIa of the invention on the insoluble support include acetate buffer, phosphate buffer, MES (2-Morpholinoethanesulfonic acid) buffer, HEPES (2-[4-(2-Hydroxyethyl)-1-piperazinyl] ethanesulfonic acid) buffer, Tris buffer and borate buffer. The reaction temperature for immobilization may be appropriately set in a temperature range from 5° C. to 50° C., and is preferably in the range of 10° C. to 35° C., from the viewpoint, of the reactivity of the active groups and the stability of the Fc-binding protein or human FcγRIIIa of the invention.

For purification of an antibody with sugar chains using an adsorbent of the invention obtained by immobilizing the Fc-binding protein or human FcγRIIIa of the invention on an insoluble support, for example, a buffering solution containing an antibody with sugar chains may be added to a column packed with an adsorbent of the invention, using delivery means such as a pump, specifically adsorbing the antibody with sugar chains onto the adsorbent of the invention, and then a suitable eluent may be added to the column to elute the antibody with sugar chains. The antibody with sugar chains that can be purified by an adsorbent of the invention may be an antibody including at least the Fc region of the antibody with sugar chains, having affinity with Fc-binding protein or an Fc receptor such as FcγRIIIa. As examples there may be mentioned chimeric antibodies, humanized antibodies and human antibodies commonly used as antibodies for antibody drugs, as well as their amino acid-substituted forms. In addition, antibodies with artificially modified structures, such as bispecific antibodies, fusion antibodies between the Fc region of the antibody with sugar chains and another protein, or conjugates of the Fc region of the antibody with sugar chains with a drug (ADC) can also be purified by the adsorbent of the invention. Before adding the buffering solution containing the antibody with sugar chains to the column, the column is preferably equilibrated using an appropriate buffering solution to allow purification of the antibody with sugar chains to a higher purity. Examples for the buffering solution include buffering solutions with inorganic salts as components, such as phosphate buffer, where the pH of the buffering solution is pH 3 to 10 and preferably pH 5 to 8.

For elution of the antibody with sugar chains that has been adsorbed onto the adsorbent of the invention, it is sufficient to weaken the interaction between the antibody with sugar chains and the ligand (the Fc-binding protein or human FcγRIIIa of the invention), and specifically, this may be by changing the pH with the buffering solution, or using a counter peptide, changing the temperature or changing the salt concentration. A specific example of an eluent for elution of the antibody with sugar chains that has been adsorbed on the adsorbent of the invention is a buffering solution that is more toward the acidic end than the solution used for adsorption of the antibody with sugar chains onto the adsorbent of the invention. Examples of types of buffering solutions include citrate buffer, glycine hydrochloride buffer and acetate buffer, having buffer capacity at the acidic end. The pH of the buffering solution may be set within a range that does not impair the function of the antibody, and it is preferably pH 2.5 to 6.0, more preferably pH 3.0 to 5.0 and even more preferably pH 3.3 to 4.0.

When the antibody is to be purified from a solution containing the antibody with sugar chains using the adsorbent of the invention, the point of elution (elution fraction) of the antibody will differ depending on the difference in antibody sugar chain structures. By thus separating the antibodies using an adsorbent of the invention it is possible to identify differences in sugar chain structures of antibodies. There are no particular restrictions on the structures of sugar chains that can be identified, and as examples, there may be mentioned sugar chains added when expressing antibodies in animal cells such as CHO cells, or yeast such as *Pichia* yeast or *Saccharomyces* yeast, as the host, sugar chains on human antibodies, or sugar chains added to antibodies by chemical synthesis methods. The adsorbent of the invention may also be utilized for isolation of the sugar chains themselves, since they can be isolated based on differences in the sugar chains structures of the antibodies.

While it was explained above that differences in the sugar chain structures of antibodies can be identified by the adsorbent of the invention, differences in sugar chain structures can likewise be identified when using Fc receptors other than FcγRIIIa ((FcγRI, FcγRIIa, FcγRIIb, FcγRIIIb or FcRn) as the ligand protein used in the adsorbent.

Advantageous Effect of Invention

The Fc-binding protein of the invention is a protein wherein an amino acid residue at a specific position in the extracellular domain of human FcγRIIIa has been substituted with another amino acid residue. The Fc-binding protein of the invention has increased stability against heat and acids, compared to the wild type human FcγRIIIa. Thus, the Fc-binding protein of the invention is useful as the ligand of an adsorbent for isolation of immunoglobulins.

In addition, the invention relates to an adsorbent obtained by immobilizing human FcγRIIIa on an insoluble support, the adsorbent specifically adsorbing an antibody with sugar chains among antibodies, thereby allowing easy identification of the presence or absence of sugar chain addition on an antibody, which has been difficult in the past. By using an adsorbent of the invention it is possible to specifically purify an antibody with sugar chains, thereby allowing efficient production of an antibody with sugar chains.

BRIEF DESCRIPTION OF DRAWINGS

FIG. 4 is a chromatographic chart showing elution of an antibody using FcR5a-immoblizing gel. In the graph, Fr represents the location of the recovered fraction.

FIG. 5 is a table listing sugar chain structures added to antibodies. In the table, N1 to N8 correspond to N1 to N8 in Table 10, while M1 and M2 correspond to M1 and M2 in Table 11.

FIG. 8 is a set of graphs comparing the affinity of human FcγRIIIa and Protein. A for sugar chain-hearing human IgG1 and sugar chain-removed human IgG1. (A) shows the results for human FcγRIIIa, and (B) shows the results for Protein A.

EXAMPLES

Figure 1:
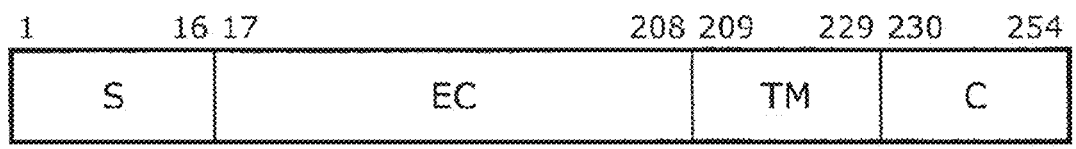
FIG. 1 is an schematic diagram of human. FcγRIIIa. The numerals in the diagram represent the amino acid sequence positions in SEQ ID NO: 1. Also in the diagram, S represents the signal sequence, EC represents the extracellular domain, TM represents the transmembrane region and C represents the cytoplasmic region.

Examples will now be provided for further explanation of the invention, with the understanding that the invention is not limited to these examples.

Example 1

Preparation of Fc-Binding Protein or Human FcγRIIIa Expression Vector (1) A nucleotide sequence with codons converted from the human type to the *E. coli* type, was designed based on the amino acid sequence from glycine (Gly) at position 17 to glutamine (Gln) at position 192 of the amino acid sequence of human FcγRIIIa of SEQ ID NO: 1, by using the DNA-works method (Nucleic Acids Res., 30, e43, 2002). The designed nucleotide sequence is SEQ ID NO: 2.

(2) For construction of a polynucleotide including the sequence of SEQ ID NO: 2, oligonucleotides consisting of the sequences of SEQ ID NO: 3 to 20 were synthesized, and the oligonucleotides were used for the two-step PCR described below.

(2-1) In the first step of the PCR, a reaction mixture with the composition shown in Table 1 was prepared and the reaction mixture was heat treated at 98° C. for 5 minutes, after which 10 cycles of reaction were repeated, where one cycle consisted of a first step at 98° C. for 10 seconds, a second step at 62° C. for 5 seconds and a third step at 72° C. for 90 seconds, to synthesize a polynucleotide, which was designated as FcRp1. The "DNA mix" in Table 1 is a mixed solution of the 18 different oligonucleotides comprising the sequences of SEQ ID NO: 3 to 20, each sampled in a fixed amount.

TABLE 1

| Composition | Concentration/volume |
| --- | --- |
| DNA mix (SEQ ID NO: 3 to 20) | 2.5 mM each |
| 5 × Prime STAR buffer (Takara Bio, Inc.) | 10 μL |
| 2.5 mM dNTPs | 4 μL |
| 2.5 U/μL Prime STAR HS (Takara Bio, Inc.) | 0.5 μL |
| H$_2$O | Up to 50 μL |

(2-2) In the second step of the PCR, the FcRp1 synthesized in (2-1) was used as template and the oligonucleotides comprising the sequences of SEQ ID NO: 21 (5'-TAGC-CATGGGCATGCGTACCGAAGATCTGCCGAAAGC-3') and SEQ ID NO: 22 (5'-CCCAAGCTTAATGATGATGAT-GATGATGGCCCCCTTGGGTAATGGTAATATTCACGG TCTCGCTGC-3') were used as PCR primers. Specifically, a reaction mixture with the composition shown in Table 2 was prepared and the reaction mixture was heat treated at 98° C. for 5 minutes, after which 30 cycles of reaction were repeated, where one cycle consisted of a first step at 98° C. for 10 seconds, a second step at 62° C., for 5 seconds and a third step at 72° C. for 1.5 minutes.

TABLE 2

| Composition | Concentration/volume |
| --- | --- |
| Template DNA | 2 μL |
| Forward primer | 0.4 μM |
| Reverse primer | 0.4 μM |
| 5 × Prime STAR buffer (Takara Bio, Inc.) | 10 μL |
| 2.5 mM dNTPs | 4 μL |
| 2.5 U/μL Prime STAR HS (Takara Bio, Inc.) | 0.5 μL |
| H$_2$O | Up to 50 μL |

(3) The polynucleotide obtained in (2) was purified and digested with restriction enzymes NcoI and HindIII, and ligated with the expression vector pETMalE that had been previously digested with restriction enzymes NcoI and HindIII (Japanese Unexamined Patent Publication No. 2011-206046), and the ligation product was used for transformation of *E. coli* BL21 (DE3).

(4) The obtained transformants were cultured in LB medium containing 50 μg/mL kanamycin, and then a QIAprep Spin Miniprep kit (product of Qiagen Inc.) was used for extraction of the expression vector pET-eFcR.

(5) From the expression vector pET-eFcR constructed in (4), the polynucleotide coding for human FcγRIIIa and its surrounding regions were supplied for cycle sequencing reaction using a Big Dye Terminator Cycle Sequencing Ready Reaction kit (product of Life Technologies Corp.) based on the chain terminator method, and the nucleotide sequence was analyzed with a fully automatic DNA sequencer, ABI Prism 3700 DNA analyzer (product of Life Technologies Corp.). For the analysis, oligonucleotides comprising the sequences of SEQ ID NO: 23 (5'-TAATAC-GACTCACTATAGGG-3') or SEQ ID NO: 24 (5'-TAT-GCTAGTTATTGCTCAG-3') were used as the sequencing primers.

The amino acid sequence of the polypeptide expressed in expression vector pET-eFcR is of SEQ ID NO: 25, and the sequence of the polynucleotide coding for that polypeptide is of SEQ ID NO: 26, In SEQ ID NO: 25, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the extracellular domain of the human FcγRIIIa (the region from position 17 to position 192 of SEQ ID NO: 1), the region of glycine (Gly) from position 209 to position 210 is the linker sequence, and the region of histidine (His) from position 211 to position 216 is the tag sequence.

Example 2

Mutagenesis in Fc-Binding Protein and Construction of Library

For the Fc-binding protein expression vector pER-eFcR constructed in Example 1, mutation transfer was conducted randomly by error-prone PCR in the polynucleotide portion coding for the Fc-binding protein.

(1) Error-prone PCR was conducted using pET-eFcR constructed in Example 1 as template. The error-prone PCR was carried out by preparing a reaction mixture with the composition shown in Table 3, and then heat treating the reaction mixture at 95° C. for 2 minutes, carrying out 35 cycles of reaction where one cycle consisted of a first step at 95° C. for 30 seconds, a second step at 60° C. for 30 seconds and a third step at 72° C. for 90 seconds, and finally conducting heat treatment at 72° C. for 7 minutes. As a result of the error-prone PCR, mutations were satisfactorily introduced into the polynucleotide coding for Fc-binding protein, with an average mutagenesis rate of 1.26%.

TABLE 3

| Composition | Concentration/volume |
|---|---|
| Template DNA (pET-eFcR) | 0.12 ng/μL |
| 10 μM PCR primer (SEQ ID NO: 21) | 4 μL |
| 10 μM PCR primer (SEQ ID NO: 22) | 4 μL |
| 2.5 mM MgCl$_2$ | 12 μL |
| 10 mM dATP | 2 μL |
| 10 mM dGTP | 2 μL |
| 10 mM dCTP | 10 μL |
| 10 mM dTTP | 10 μL |
| 10 mM MnCl$_2$ | 4 μL |
| 10 × Ex Taq Buffer (Takara Bio, Inc.) | ×1 |
| Go Taq Polymerase (Promega Corp.) | 1 μL |
| H$_2$O | Up to 100 μL |

(2) After purifying the PCR product obtained in (1), it was digested with restriction enzymes NcoI and HindIII, and ligated with expression vector pETMalE that had been previously digested with the same restriction enzymes (Japanese Unexamined Patent Publication No. 2011-206046).

(3) Upon completion of the ligation reaction, the reaction mixture was introduced into *E. coli* BL21(DE3) by an electroporation method, and culturing was conducted. (at 37° C. for 18 hours) on LB plate culture medium containing 50 μg/mL kanamycin, after which the colonies formed on the plate were used as a random mutant library.

Example 3

Screening of Heat-Stabilized Fc-Binding Protein (1) The random mutant library (of transformants) prepared in Example 2 was inoculated into 200 μL of 2YT liquid medium. (16 g/L peptone, 10 g/L yeast extract, 5 g/L sodium chloride) containing 50 μg/mL kanamycin, and a 96-well deep well plate was used for shake culturing overnight at 30° C.

(2) After culturing, 5 μL of culture solution was inoculated into 50 μg/mL of 2YT liquid medium containing 0.05 mM IPTG (isopropyl-β-D-thiogalactopyranoside), 0.3% glycine and 50 μg/mL kanamycin, and a 96-well deep well plate was used for shake culturing overnight at 20° C.

(3) After culturing, the culture supernatant obtained by centrifugation was diluted 2-fold with 20 mM Tris-HCl buffering solution (pH 7.4) containing 150 mM sodium chloride. The diluted solution was heat treated at 45° C. for 10 minutes.

(4) The antibody binding activity of the Fc-binding protein after the heat treatment of (3) and the antibody binding activity of the Fc-binding protein without the heat treatment of (3) were each measured by the ELISA method described below, and the antibody binding activity of the Fc-binding protein after heat treatment was divided by the antibody binding activity of the Fc-binding protein without heat treatment to calculate the residual activity.

(4-1) A gammaglobulin preparation (by Kaketsuken) as the human antibody, was immobilized in the wells of a 96-well microplate at 1 μg/well (at 4° C. for 18 hours), and after complete immobilization, blocking was performed with 20 mM Tris-HCl buffering solution (pH 7.4) containing 2% (w/v) SKIM MILK (product of BD) and 150 mM sodium chloride.

(4-2) After wash with rinsing buffer (20 mM Tris-HCl buffer (pH 7.4) containing 0.05%[w/v] Tween 20 and 150 mM NaCl), a solution containing Fc-binding protein for evaluation of the antibody binding activity was added, and reaction was conducted between the Fc-binding protein and the immobilized gammaglobulin (at 30° C. for 1 hour).

(4-3) Upon completion of the reaction, it was rinsed with wash buffer, and anti-6His antibody (product of Bethyl Laboratories) diluted to 100 ng/mL was added at 100 μL/well.

(4-4) Reaction was conducted at 30° C. for 1 hour, and after wash with rinsing buffer, IME Peroxidase Substrate (product of KPL) was added at 50 μL/well. Coloration was stopped by adding 1M phosphoric acid at 50 μL/well, and the absorbance at 450 nm was measured with a microplate reader (product of Tecan).

(5) Approximately 2700 transformants were evaluated by the method of (4), and among these there were selected transformants expressing Fc-binding protein and having increased thermal stability compared to the wild type Fc-binding protein (without amino acid substitutions). The selected transformants were cultured, and an expression vector was prepared using a QIAprep Spin Miniprep kit (product of Qiagen Inc.).

(6) The nucleotide sequence of the polynucleotide region coding for Fc-binding protein, inserted into the obtained expression vector, was analyzed by the same method described in Example 1 (5), and the amino acid mutation sites were identified.

Table 4 shows a summary of the amino acid substitution positions with respect to the wild type Fc-binding protein (without amino acid substitution), in the Fc-binding protein expressed by the transformants selected in (5), as well as the post-heat treatment residual activities (%). An Fc-bindinq protein including the amino acid residues from glycine at position 17 to glutamine at position 192, of the amino acid sequence of SEQ ID NO: 1, and having at least one amino acid substitution from among Met18Arg (a designation indicating that the methionine at position 18 of SEQ ID NO: 1 is substituted by arginine, same hereunder), Val27Glu, Phe29Leu, Phe20Ser, Leu30Gln, Tyr35Asn, Tyr35Asp, Tyr35Ser, Tyr35His, Lys46Ile, Lys46Thr, Gln48His, Gln48Leu, Ala50His, Tyr51Asp, Tyr51His, Glu54Asp, Glu54Gly, Asn56Thr, Gln59Arg, Phe61Tyr, Glu64Asp, Ser65Arg, Ala71Asp, Phe75Leu, Phe75Ser, Phe75Tyr, Asp77Asn, Ala78Ser, Asp82Glu, Asp82Val, Gln90Arg, Asn92Ser, Leu93Arg, Leu93Met, Thr95Ala, Thr95Ser, Leu110Gln, Arg115Gln, Trp116Leu, Phe118Tyr, Lys119Glu, Glu120Val, Glu121Asp, Glu121Gly, Phe151Ser, Phe151Tyr, Ser155Thr, Thr163Ser, Ser167Gly, Ser169Gly, Phe171Tyr, Asn180Lys, Asn180Ser, Asn180Ile, Thr185Ser and Gln192Lys, among the amino acid residues from position 17 to position 192, can be said to have increased thermal stability compared to the wild type Fc-binding protein.

TABLE 4

| Amino acid-substituted | Residual activity (%) | Amino acid-substituted | Residual activity (%) |
| --- | --- | --- | --- |
| Lys46Ile | 33.6 | Tyr35His, Ser155Thr | 65.8 |
| Gln59Arg | 59.6 | Tyr35Asn, Ser169Gly | 44.8 |
| Phe61Tyr | 48.2 | Lys46Thr, Asn92Ser | 57.6 |
| Glu64Asp | 45.1 | Ala50His, Thr95Ser | 65.3 |
| Phe75Ser | 47.3 | Tyr51His, Thr95Ser | 56.5 |
| Asp82Glu | 43.1 | Asp77Asn, Ala78Ser | 51.7 |
| Asn92Ser | 55.5 | Gln90Arg, Asn92Ser | 58.8 |
| Leu93Met | 42.9 | Phe151Ser, Asn180Lys | 33.0 |
| Glu121Asp | 46.2 | Phe29Ser, Gln90Arg, Thr163Ser | 46.1 |
| Thr163Ser | 33.2 | Phe29Leu, Trp116Leu, Phe118Tyr | 81.0 |
| Asn180Ser | 43.6 | Tyr35Asn, Gln48Leu, Leu110Gln | 74.6 |
| Asn180Ile | 50.6 | Tyr35Ser, Phe151Tyr, Ser167Gly | 45.0 |
| Thr185Ser | 39.3 | Tyr35Asn, Glu120Val, Gln192Lys | 75.1 |
| Met18Arg, Glu64Asp | 53.3 | Gln48Leu, Phe75Tyr, Arg115Gln | 38.9 |
| Val27Glu, Tyr35Asn | 96.0 | Tyr51Asp, Phe75Leu, Glu121Gly | 94.8 |
| Phe29Leu, Asn56Thr | 38.5 | Ala71Asp, Phe75Leu, Glu121Gly | 93.9 |
| Phe29Ser, Thr95Ala | 58.7 | Tyr35Asp, Glu54Gly, Asp82Val, Lys119Glu | 63.0 |
| Phe29Leu, Phe118Tyr | 56.6 | Gln48His, Ser65Arg, Leu93Arg, Phe171Tyr | 44.7 |
| Leu30Gln, Tyr35Asn | 88.1 | Wild type | 31.3 |
| Tyr35His, Glu54Asp | 67.1 | | |

Of the amino acid-substituted Fc-binding proteins shown in Table 4, the Fc-binding protein. exhibiting the highest remaining activity, having the amino acid substitutions Val27Glu and Tyr35Asn, was designated as FcR2, and the expression vector containing the polynucleotide coding for FcR2 was designated as pET-FcR2, The amino acid. sequence of FcR2 is of SEQ ID NO: 27, and the sequence of the polynucleotide coding for FcR2 is of SEC) ID NO: 28. In SEQ ID NO: 27, the region from methionine (Met) at position 1 to alanine (Ala) at position 26 is the MalE signal peptide, the region from lysine (Lys) at position. 27 to methionine (Met) at position 32 is the linker sequence, the region from caycine (Gly) at position 33 to glutamine (Gln) at position 208 is the amino acid sequence of FcR2 (corresponding to the region from position 17 to position 192 of SEQ ID NO: 1), the region of glycine (Gly) from position 209 to position 210 is the linker sequence, and the region of histidine (His) from position 211 to position 216 is the tag sequence. Also, in SEQ ID NO: 27, the glutamic acid of Val27Glu is at position 43, and the asparagine of Tyr35Asn is at position 51.

Example 4

Construction of Amino Acid-Substituted Fc-Binding Protein

Even greater increased stability was attempted by accumulating amino acid substitutions related to increased thermal stability of Fc-binding protein as demonstrated in Example 3. The accumulation of substituted amino acids was accomplished mainly using PCR, and the 7 types of Fc-binding proteins described by (a) to (g) below were constructed. (a) FcR3 further having the amino acid substitution Phe75Leu in FcR2

(b) FcR4 further having the amino acid. substtutions Phe75Leu and Glu121Gly in FcR2

(c) FcR5a further having the amino acid substitution Asn92Ser in FcR4

(d) FcR5b further having the amino acid substitution Glu54Asp in FcR4

(e) FcR6a further having the amino acid substitution Glu54Asp in FcR5a (f) FcR6b further having the amino acid substitution Glu120Val in FcR5b (g) FcR7 further having the amino acid substitution Glu120Val in FcR6a The method for constructing each Fc-binding protein. will now be described in detail.

(a) FcR3

Val27Glu, Tyr35Asn and Phe75Leu were selected among the amino acid substitutions relating to increased thermal stability as demonstrated in Example 3, and FcR3 having these substitutions accumulated in the wild type Fc-binding protein was constructed. Specifically, FcR3 was constructed by mutagenesis in which Phe75Leu was introduced into the polynucleotide coding for FcR2.

(a-1) PCR was conducted using the pET-FcR2 obtained in Example 3 as template. The primers used for the PCR were oligonucleotides having the sequences of SEQ ID NO: 24 and SEQ ID NO: 29 (5′-AGCCAGGCGAGCAGCTACCT-TATTGATGCG-3′). The PCR was carried out by preparing a reaction mixture with the composition shown in Table 5, and then heat treating the reaction mixture at 98° C. for 5 minutes, carrying out 30 cycles of reaction where one cycle consisted of a first step at 98° C. for 10 seconds, a second step at 55° C. for 5 seconds and a third step at 72° C. for 1 minute, and finally conducting heat treatment at 72° C. for 7 minutes. The amplified PCR product was supplied to agarose gel electrophoresis and purified from the gel using a QIAquick Gel Extraction kit (product of Qiagen Inc.). The purified PCR product was designated as m3F.

TABLE 5

| Composition | Concentration/volume |
| --- | --- |
| Template DNA | 2 μL |
| 10 μM Forward primer | 1 μL |
| 10 μM Reverse primer | 1 μL |
| 5 × Prime STAR buffer (Takara Bio, Inc.) | 4 μL |
| 2.5 mM dNTPs | 2 μL |
| 2.5 U/μL Prime STAR HS (Takara Bio, Inc.) | 0.5 μL |
| H$_2$O | Up to 20 μL |

(a-2) This was conducted in the same manner as (a-1), using the pET-FcR2 obtained in Example 3 as template, and except that the PCR primers were oligonucleotides comprising the sequences of SEQ ID NO: 23 and SEQ ID NO: 30 (5T-CCACCGTCGCCGCATCAATAAGGTAGCTGC-3′). The purified PCR product was designated as m3R.

(a-3) The two PCR products obtained in (a-1) and (a-2) (m3F and m3R) were mixed to prepare a reaction mixture having the composition shown in Table 6. The reaction mixture was then heat treated at 98° C. for 5 minutes, and then PCR was conducted with 5 cycles of reaction where one cycle consisted of a first step at 98° C. for 10 seconds, a second step at 55° C. for 5 seconds and a third step at 72° C. for 1 minute, to obtain a PCR product m3p comprising m3S and m3R in linkage.

TABLE 6

| Composition | Concentration/ volume |
|---|---|
| PCR product | Equimolar |
| 2.5 U/μL Prime STAR HS (Takara Bio, Inc.) | 0.5 μL |
| 5 × Prime STAR buffer (Takara Bio, Inc.) | 4 μL |
| 2.5 mM dNTPs | 2 μL |
| H₂O | Up to 20 μL |

(a-4) The PCR product m3p obtained in (a-3) was used as template for PCR, using oligonucleotides comprising the sequences of SEQ ID NO: 23 and of SEQ ID NO: 24 as the PCR primers. The PCR was carried out by preparing a reaction mixture with the composition shown in Table 7, and then heat treating the reaction mixture at 98° C. for 5 minutes, and conducting 30 cycles of reaction, where one cycle consisted of a first step at 98° C. for 10 seconds, a second step at 55° C. for 5 seconds and a third step at 72° C. for 1 minute. Thus was constructed a polynucleotide coding for FcR3 having one amino acid substitution introduced, into FcR2.

TABLE 7

| Composition | Concentration/ volume |
|---|---|
| PCR product | 2 μL |
| 10 μM Forward primer | 2 μL |
| 10 μM Reverse primer | 2 μL |
| 5 × Prime STAR buffer (Takara Bio, Inc.) | 10 μL |
| 2.5 mM dNTPs | 4 μL |
| 2.5 U/μL Prime STAR HS (Takara Bio, Inc.) | 1 μL |
| H₂O | Up to 50 μL |

(a-5) The polynucleotide obtained in (a-4) was purified and then digested with restriction enzymes NcoI and HindIII and ligated with the expression vector pETMalE previously digested with restriction enzymes NcoI and HindIII (Japanese Unexamined Patent Publication No. 2011-206046), and the ligation product was used for transformation of *E. coli* B121 (DE3).

(a-6) The obtained transformants were cultured on LB medium containing 50 μg/mL kanamycin. By extracting the plasmids from the recovered cells (transformants), there was obtained plasmid pET-FcR3 containing a polynucleotide coding for FcR3, which was a polypeptide with amino acid substitutions at 3 locations of the wild type Fc-binding protein.

(a-7) Analysis of the nucleotide sequence of pET-FcR3 was conducted by the same method as Example 1 (5).

The amino acid sequence of FcR3 with the signal sequence and polyhistidine tag added is of SEQ ID NO: 31, and the sequence of the polynucleotide coding for FcR3 is of SEQ ID NO: 32. In SEQ ID NO: 31, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR3 (corresponding to the region from position 17 to position 192 of SEQ ID NO: 1), the region of glycine (Gly) from position 209 to position. 210 is the linker sequence, and the region of histidine (His) from position 211 to position 216 is the tag sequence. Also, in SEQ ID NO: 31, the glutamic acid of Val27Glu is at position 43, the asparagine of Tyr35Asn is at position 51, and the leucine of Phe75Leu is at position 91.

(b) FcR4

Val27Glu, Tyr35Asn, Phe75Leu and Glu121Gly were selected among the amino acid substitutions relating to increased stability of Fc-binding protein as demonstrated in Example 3, and FcR4 having these substitutions accumulated in the wild type Fc-binding protein was constructed. Specifically, FcR4 was constructed by mutagenesis in which Phe75Leu and Glu121Gly were introduced into the polynucleotide coding for FcR2.

(b-1) The PCR product m3F was obtained by the same method as (a-1). Also, a plasmid expressing Fc-binding protein including the amino acid substitutions Ala71Asp, Phe75Leu and Glu121Gly, obtained in Example 3 (Table 4) was used as template and oligonucleotides comprising the sequences of SEQ ID NO: 24 and SEQ ID NO: 29 were used as PCR primers, for PCR by the same method as in (a-1), to obtain PCR product m4R.

(b-2) After mixing the two PCR products obtained in (b-1) (m3F and m4R), PCR was conducted in the same manner as (a-3), and m3F and m4R were linked. The obtained PCR product was designated as m4p.

(b-3) The PCR product m4p obtained in (b-2) was used as template, and oligonucleotides comprising the sequences of SEQ ID NO: 23 and SEQ ID NO: 2-1 were used as PCR primers, for PCR by the same method as (a-4). Thus was constructed a polynucleotide coding for FcR4.

(b-4) The polynucleotide obtained in (b-3) was purified and then digested with restriction enzymes NcoI and HindIII and ligated with the expression vector pETMalE that had been previously digested with restriction enzymes NcoI and HindIII (Japanese Unexamined Patent Publication No. 2011-206046), and the ligation product was used for transformation of *E. coli* BL21 (DE3).

(b-5) The obtained transformants were cultured on LB medium containing 50 μg/mL kanamycin. By extracting the plasmids from the recovered cells (transformants), there was obtained plasmid pET-FcR4 containing a polynucleotide coding for FcR4, which was a polypeptide with amino acid substitutions at 4 locations of the wild type Fc-binding protein.

(b-6) Analysis of the nucleotide sequence of pET-FcR4 was conducted by the same method as Example 1 (5).

The amino acid sequence of FcR4 with the signal sequence and polyhistidine tag added is of SEQ ID NO: 33, and the sequence of the polynucleotide coding for FcR4 is of SEQ. ID NO: 34. In SEQ ID NO: 33, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR4 (corresponding to the region from position 17 to position 192 of SEQ ID NO: 1), the region of glycine (Gly) from position 209 to position. 210 is the linker sequence, and the region of histidine (His) from position. 211 to position 216 is the tag sequence. Also, in SEQ ID NO: 33, the glutamic acid of Val27Glu is at position 43, the asparagine of Tyr35Asn is at position 51, the leucine of Phe75Leu is at position 91 and the glycine of Glu121Gly is at position 137.

(c) FcR5a

Val27Glu, Tyr35Asn, Phe75Leu, Asn92Ser and Glu121Gly were selected among the amino acid substitutions relating to increased stability of Fc-binding protein as demonstrated in Example 3, and FcR5a having these substitutions accumulated in the wild type Fc-binding protein was constructed. Specifically, FcR5a was constructed by mutagenesis in which Asn92Ser was introduced into the polynucleotide coding for FcR4 constructed in (b).

(c-1) PCR was conducted by the same method as (a-1), except that pET-FcR4 constructed in (b) was used as template and oligonucleotides comprising the sequences of SEQ ID NO: 22 and SEQ. ID NO: 35 (5'-GAATATCGTTGCCA-GACCAGCCTGAGCACC-3') were used as PCR primers. The purified. PCR product was designated as m5aF.

(c-2) PCR was conducted by the same method as (a-1), except that pET-FcR4 constructed in (b) was used as template and oligonucleotides comprising the sequences of SEQ ID NO: 21 and SEQ ID NO: 36 (5'-GATCGCTCAGG-GIGCTCAGGCTGGTCTGGC-3' were used as PCR primers. The purified PCR product was designated as m5aR.

(c-3) After mixing the two PCR products obtained in (c-1) and (c-2) (m5aF and m5aR), PCR was conducted in the same manner as (a-3), and m5aF and m5aR were linked. The obtained PCR product was designated as m5ap.

(c-4) The PCR product m5ap obtained in (c-3) was used as template, and oligonucleotides comprising the sequences of SEQ ID NO: 21 and of SEQ ID NO: 22 were used as PCR primers, for PCR by the same method as (a-4). Thus was constructed a polynucleotide coding for FcR5a.

(c-5) The polynucleotide obtained in (c-4) was purified and then digested with restriction enzymes NcoI and HindIII and ligated with the expression vector pETMalE that had been previously digested with restriction enzymes NcoI and HindIII (Japanese Unexamined Patent Publication No. 2011-206046), and the ligation product was used for transformation of E. coli B121 (DE3).

(c-6) The obtained transformants were cultured on LB medium containing 50 μg/mL kanamycin. By extracting the plasmids from the recovered cells (transformants), there was obtained plasmid pET-FcR5a containing a polynucleotide coding for FcR5a, which was a polypeptide with amino acid substitutions at 5 locations of the wild type Fc-binding protein.

(c-7) Analysis of the nucleotide sequence of pET-FcR5a was conducted by the same method as Example 1 (5).

The amino acid sequence of FcR5a with the signal sequence and polyhistidine tag added is of SEQ ID NO: 37, and the sequence of the polynucleotide coding for FcR5a is of SEQ ID NO: 38. In SEQ ID NO: 37, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR5a (corresponding to the region from position 17 to position 192 of SEQ ID NO: 1), the region of glycine (Gly) from position 209 to position 210 is the linker sequence, and the region of histidine (His) from position 211 to position 216 is the tag sequence. Also, in SEQ ID NO: 37, the glutamic acid of Val27Glu is at position 43, the asparagine or Tyr35Asn is at position 51, the leucine of Phe75Leu is at position 91, the serine of Asn92Ser is at position 108 and the glycine of Glu121Gly is at position 137.

(d) FcR5b

Val27Glu, Tyr35Asn, Glu54Asp, Phe75Leu and Glu121Gly were selected among the amino acid substitutions relating to increased stability of Fc-binding protein as demonstrated in Example 3, and FcR5b having these substitutions accumulated in the wild type Fc-binding protein was constructed. Specifically, FcR5b was constructed by mutagenesis in which Glu54Asp was introduced into the polynucleotide coding for FcR4 constructed in (b).

(d-1) PCR was conducted by the same method as (a-1), except that pET-FcR4 constructed in (b) was used as template and oligonucleotides comprising the sequences of SEQ ID NO: 22 and SEQ. ID NO: 39 (5'-CAGGGCGCG-TATAGCCCGGATGATAACAGC-3') were used as PCR primers. The purified. PCR product was designated as m5bF.

(d-2) PCR was conducted by the same method as (a-1), except that pET-FcR4 constructed in (b) was used as template and oligonucleotides comprising the sequences of SEQ ID NO: 21 and SEQ ID NO: 40 (5'-CACTGGGTGCTGI-TATCATCCGGGCTATAC-3') were used as PCR primers. The purified PCR product was designated as m5bR.

(d-3) After mixing the two PCR products obtained in (d-1) and (d-2) (m5bF and m5bR), PCR was conducted in the same manner as (a-3), and m5bF and m5bR were linked. The obtained PCR product was designated as m5bp.

(d-4) The PCR product m5bp obtained in (d-3) was used as template, and oligonucleotides comprising the sequences of SEQ ID NO: 21 and of SEQ ID NO: 22 were used as 5CR primers, for 5CR by the same method as (a-4). Thus was constructed a polynucleotide coding for FcR5b.

(d-5) The polynucleotide obtained in (d-4) was purified and then digested with restriction enzymes NcoI and HindIII and ligated with the expression vector pETMalE previously digested with restriction enzymes NcoI and HindIII (Japanese Unexamined Patent Publication No. 2011-206046), and the ligation product was used for transformation of E. coli BL21 (DE3).

(d-6) The obtained transformants were cultured on LB medium containing 50 μg/mL kanamycin. By extracting the plasmids from the recovered cells (transformants), there was obtained plasmid pET-FcR5b containing a polynucleotide coding for FcR5b, which was a polypeptide with amino acid substitutions at 5 locations of the wild type Fc-binding protein.

(d-7) Analysis of the nucleotide sequence of pET-FcR5b was conducted by the same method as Example 1 (5).

The amino acid sequence of FcR5b with the signal sequence and polyhistidine tag added is shown as SEQ ID NO: 41, and the sequence of the polynucleotide coding for FcR5b is shown as SEQ ID NO: 42. In SEC) ID NO: 41, the region from methionine (Met) at position 1 to alanine (Ala) at position 26 is the MalE signal peptide, the region from lysine (Lys) at position 27 to methionine (met) at position 32 is the linker sequence, the region from glycine (Gly) at position 33 to glutamine (Gln) at position 208 is the amino acid sequence of FcR5b (corresponding to the region from position 17 to position 192 of SEQ ID NO: 1), the region of glycine (Gly) from position 209 to position 210 is the linker sequence, and the region of histidine (His) from position 211 to position 216 is the tag sequence. Also, in SEQ ID NO 41, the glutamic acid of Val27Glu is at position 43, the asparagine of Tyr35Asn is at position 51, the aspartic acid of Glu54Asp is at position 70, the leucine of Phe75Leu is at position 91 and the glycine of Glu121Gly is at position 137.

(e) FcR6a.

Val27Glu, Tyr35Asn, Glu54Asp, Phe75Leu, Asn92Ser and Glu121Gly were selected among the amino acid substitutions relating to increased stability of Fc-binding protein as demonstrated in Example 3, and FcR6a having these substitutions accumulated in the wild type Fc-binding protein was constructed. Specifically, FcR6a was constructed by mutagenesis in which Glu54Asp was introduced into the polynucleotide coding for FcR5a constructed in (c).

(e-1) PCR was conducted by the same method as (a-1), except that pET-FcR5a constructed in (c) was used as template and oligonucleotides comprising the sequences of SEQ ID NO: 22 and SEQ ID NO: 39 were used as PCR primers. The purified PCR product was designated as m6aF.

(e-2) PCR was conducted by the same method as (a-1), except that pET-FcR4 constructed in (b) was used as template and oligonucleotides comprising the sequences of SEQ ID NO: 21 and SEQ ID NO: 40 were used as PCR primers. The purified PCR product was designated as m6aR.

(e-3) After mixing the two PCR products obtained in (e-1) and (e-2) (m6aF and m6aR), PCR was conducted in the same manner as (a-3), and m6aF and m6aR were linked. The obtained PCR product was designated as m6ap.

(e-4) The PCR product m6ap obtained in (e-3) was used as template, and oligonucleotides comprising the sequences of SEQ ID NO: 21 and of SEQ ID NO: 22 were used as PCR primers, for PCR by the same method as (a-4) Thus was constructed a polynucleotide coding for FcR6a.

(e-5) The polynucleotide obtained in (e-4) was purified and then digested with restriction enzymes NcoI and HindIII and ligated with the expression vector pETMalE previously digested with restriction enzymes NcoI and HindIII (Japanese Unexamined Patent Publication No. 2011-206046), and the ligation product was used for transformation of *E. coli* BL21 (DE3).

(e-6) The obtained transformants were cultured on LB medium containing 50 μg/mL kanamycin. By extracting the plasmids from the recovered cells (transformants), there was obtained plasmid pET-FcR6a containing a polynucleotide coding for FcR6a, which was a polypeptide with amino acid substitutions at 6 locations of the wild type Fc-binding protein.

(e-7) Analysis of the nucleotide sequence of pET-FcR6a was conducted by the same method as Example 1 (5).

The amino acid sequence of FcR6a with the signal sequence and polyhistidine tag added is of SEQ ID NO: 43, and the sequence of the polynucleotide coding for FcR6a is of SEQ ID NO: 44. In SEQ ID NO: 43, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR6a (corresponding to the region from position 17 to position 192 of SEQ ID NO: 1), the region of glycine (Gly) from position 209 to position 210 is the linker sequence, and the region of histidine (His) from position 211 to position 216 is the tag sequence. Also, in SEQ ID NO: 43, the glutamic acid of Val27Glu is at position 43, the asparagine of Tyr35Asn is at position 51, the aspartic acid of Glu54Asp is at position 70, the leucine of Phe75Leu is at position 91, the serine of Asn92Ser is at position 108 and the glycine of Glu121Gly is at position 137.

(f) FcR6b

Val27Glu, Tyr35Asn, Glu54Asp, Phe75Leu, Glu120Val and Glu121Gly were selected among the amino acid substitutions relating to increased stability of Fc-binding protein as demonstrated in Example 3, and FcR6b having these substitutions accumulated in the wild type Fc-binding protein was constructed. Specifically, FcR6b was constructed by mutagenesis in which Glu120Val was introduced into the polynucleotide coding for FcR5b constructed in (d).

(f-1) PCR was conducted by the same method as (a-1), except that pET-FcR5b constructed in (d) was used as template and oligonucleotides comprising the sequences of SEQ ID NO: 22 and SEQ ID NO: 45 (5-GTGT-TCAAAGTGGGGGATCCGATTCATCTG-3') were used as PCR primers. The purified PCR product was designated as m6bF.

(f-2) PCR was conducted by the same method as (a-1), except that pET-FcR5b constructed in (d) was used as template and oligonucleotides comprising the sequences of SEQ ID NO: 21 and SEQ ID NO: 46 (5'-AATCGGATC-CCCCACTTTGAACACCCACCG-3') were used as PCR primers. The purified. PCR product was designated as m6bR.

(f-3) After mixing the two PCR products obtained in (f-1) and (f-2) (m6bF and m6bR), PCR was conducted in the same manner as (a-3), and m6bF and m6bR were linked. The obtained PCR product was designated as m6bp.

(f-4) PCR was conducted by the same method as (a-4), except that the PCR product m6bp obtained in (f-3) was used as template, and oligonucleotides comprising the sequences of SEQ ID NO: 21 and of SEQ ID NO: 22 were used as PCR primers. Thus was constructed a polynucleotide coding for FcR6b.

(f-5) The polynucleotide obtained in (f-4) was purified and then digested with restriction enzymes NcoI and HindIII and ligated with the expression vector pETMalE that had been previously digested with restriction enzymes NcoI and HindIII (Japanese Unexamined Patent Publication No. 2011-206046), and the ligation product was used for transformation of *E. coli* B121 (DE3).

(f-6) The obtained transformants were cultured on LB medium containing 50 μg/mL kanamycin. By extracting the plasmids from the recovered cells (transformants), there was obtained plasmid pET-FcR6b containing a polynucleotide coding for FcR6b, which was a polypeptide with amino acid substitutions at 6 locations of the wild type Fc-binding protein.

(f-7) Analysis of the nucleotide sequence of pET-FcR6b was conducted by the same method as Example 1 (5).

The amino acid sequence of FcR6b with the signal sequence and polyhistidine tag added is of SEQ ID NO: 47, and the sequence of the polynucleotide coding for FcR6b is of SEQ ID NO: 48. In SEQ ID NO: 47, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR6b (corresponding to the region from position 17 to position 192 of SEQ ID NO: 1), the region of glycine (Gly) from position 209 to position 210 is the linker sequence, and the region of histidine (His) from position 211 to position 216 is the tag sequence. Also, in SEQ ID NO: 47, the glutamic acid of Val27Glu is at position 43, the asparagine of Tyr35Asn is at position 51, the aspartic acid of Glu54Asp is at position 70, the leucine of Phe75Leu is at position 91, the valine of Glu120Val is at position 136 and the glycine of Glu121Gly is at position 137.

(g) FcR7

Val27Glu, Tyr35Asn, Glu54Asp, Phe75Leu, Asn92Ser, Glu120Val and Glu121Gly were selected among the amino acid substitutions relating to increased stability of Fc-binding protein as demonstrated in Example 3, and FcR7 having these substitutions accumulated in the wild type Fc-binding protein was constructed. Specifically, FcR7 was constructed by mutagenesis in which Glu120Val was introduced into the polynucleotide coding for FcR6a constructed in (e.).

(g-1) PCR was conducted by the same method as (a-1), except that pET-FcR6a constructed in (e) was used as template and oligonucleotides comprising the sequences of SEQ ID NO: 22 and SEQ ID NO: 45 were used as PCR primers. The purified PCR product was designated as m7F.

(g-2) PCR was conducted by the same method as (a-1), except that pET-FcR6a constructed in (e) was used as template and oligonucleotides comprising the sequences of SEQ ID NO: 21 and SEQ ID NO: 46 were used as PCR primers. The purified PCR product was designated as m7R.

(g-3) After mixing the two PCR products obtained in (g-1) and (g-2) (m7F and m7R), PCR was conducted in the same manner as (a-3), and m7F and m7R were linked. The obtained PCR product was designated as m7p.

(g-4) PCR was conducted in the same manner as (a-4), except that the PCR product m7p obtained in (g-3) was used as template, and oligonucleotides comprising the sequences of SEQ ID NO: 21 and of SEQ ID NO: 22 were used as PCR primers. Thus was constructed a polynucleotide coding for FcR7.

(g-5) The polynucleotide obtained in (g-4) was purified and then digested with restriction enzymes NcoI and HindIII and ligated with the expression vector pETMalE that had been previously digested with restriction enzymes NcoI and HindIII (Japanese Unexamined Patent Publication No. 2011-206046), and the ligation product was used for transformation of E. coli BL21 (DE3).

(g-6) The obtained transformants were cultured on LB medium containing 50 μg/mL kanamycin. By extracting the plasmids from the recovered cells (transformants), there was obtained plasmid pET-FcR7 containing a polynucleotide coding for FcR7, which was a polypeptide with amino acid substitutions at 7 locations of the wild type Fc-binding protein.

(g-7) Analysis of the nucleotide sequence of pET-FcR7 was conducted by the same method as Example 1 (5).

The amino acid sequence of FcR7 with the signal sequence and polyhistidine tag added is of SEQ ID NO: 49, and the sequence of the polynucleotide coding for FcR7 is of SEQ ID NO: 50, In SEQ ID NO: 49, the region from methionine (Met) at position 1 to alanine (Ala) at position 26 is the MalE signal peptide, the region from lysine (Lys) at position 27 to methionine (Met) at position 32 is the linker sequence, the region from glycine (Gly) at position 33 to glutamine (Gln) at position 208 is the amino acid sequence of FcR7 (corresponding to the region from position 17 to position 192 of SEQ ID NO: 1), the region of glycine (Gly) from position 209 to position. 210 is the linker sequence, and the region of histidine (His) from position 211 to position 216 is the tag sequence. Also, in SEQ ID NO: 49, the glutamic acid of Val27Glu is at position 43, the asparagine of Tyr35Asn is at position 51, the aspartic acid of Glu54Asp is at position 70, the leucine of Phe75Leu is at position 91, the serine of Asn92Ser is at position 108, the valine of Glu120Val is at position 136, and the glycine of Glu121Gly is at position 137.

Example 5

Evaluation of Thermal Stability of Modified Fc-Binding Proteins (1) Transformants expressing the wild type Fc-binding protein prepared in Example 1, the variant Fc-binding protein selected in Example 3 (FcR2) and the variant Fc-binding proteins prepared in Example 4 (FcR3, FcR4, FcR5a, FcR5b, FcR6a, FcR6b and FcR7) were each inoculated onto 3 ml of 2YT liquid medium containing 50 μg/mL kanamycin, and aerobically shake cultured overnight at 37° C. as preculturing.

(2) This preculture solution was inoculated at 200 μL, into 20 mL of 2YT liquid medium (16 g/L peptone, 10 g/L yeast extract and 5 g/L sodium chloride) containing 50 μg/mL kanamycin, and aerobically shake cultured at 37° C.

(3) At 1.5 hours after the start of culturing, the culturing temperature was lowered to 20° C. and shake culturing was continued for 30 minutes. Next, IPTG was added to a final concentration of 0.01 mM, and aerobic shake culturing was continued overnight at 20° C.

(4) Upon completion of culturing, the cells were collected by centrifugal separation and a BugBuster Protein extraction kit (product of Takara Bio, Inc.) was used to prepare a protein extract.

(5) The antibody binding activity of the wild type Fc-binding protein and the variant Fc-binding protein in the protein extract prepared in (4) was measured by ELISA, according to Example 3 (4). A calibration curve was plotted using the extracellular domain of commercially available FcγRIIIa (4325-FC-050, by R&D Systems), and the concentration was measured.

(6) Diluton was performed with 20 mM Tris buffer (pH 7.4) containing 150 mM sodium chloride, to a concentration of 5 μg/mL for each protein. This was divided into aliquots, one of which was heat treated at 45° C. for 10 minutes using a thermal cycler (product of Eppendorf AG), and the other of which was not heat treated. The antibody binding activity of the heat-treated or non-heat-treated protein was measured by ELISA according to Example 3 (4), and the remaining activity was calculated by dividing the antibody binding activity when heat treatment was carried out by the antibody binding activity when no heat treatment was carried out.

The results are shown in Table 8. The variant Fc-binding proteins evaluated here (FcR2, FcR3, FcR4, FcR5a, FcR5b, FcR6a, FcR6b and FcR7) had higher remaining activity than the wild type Fc-binding protein, confirming that the thermal stability was increased with the variant Fc-binding proteins.

TABLE 8

| | Fc binding protein | | Remaining activity |
|---|---|---|---|
| | Designation | SEQ ID NO: | (%) |
| Example 3 | FcR2 | 27 | 37.8 |
| Example 4 (a) | FcR3 | 31 | 51.2 |
| Example 4 (b) | FcR4 | 33 | 88.1 |
| Example 4 (c) | FcR5a | 37 | 95.7 |
| Example 4 (d) | FcR5b | 41 | 93.5 |
| Example 4 (e) | FcR6a | 43 | 94.1 |
| Example 4 (f) | FcR6b | 47 | 93.6 |
| Example 4 (g) | FcR7 | 49 | 95.1 |
| Example 1 | Wild type | 25 | 27.7 |

Example 6

Evaluation of Acid Stability of Modified Fc-Binding Proteins (1) Modified Fc-binding proteins were prepared by the same method as Example 5 (1) to (5).

(2) Dilution was performed with 20 mM Tris buffer (pH 7.4) containing 150 mM sodium chloride, to a concentration of 30 μg/mL for each protein. After mixing 60 μL of each diluted Fc-binding protein and 120 μL of 0.1 M glycine hydrochloride buffer (pH 3.0), the mixture was allowed to stand at 30° C. for 2 hours.

(3) The antibody binding activity of the protein after acid treatment with glycine hydrochloride buffer (pH 3.0) and the antibody binding activity of the protein without acid treatment were measured by the ELISA method described in Example 3 (4). Next, the antibody binding activity with acid treatment was divided by the antibody binding activity without acid treatment, to calculate the residual activity.

The results are shown in Table 9. The variant Fc-binding proteins evaluated here (FcR2, FcR3, FcR4, FcR5a, FcR5b, FcR6a, FcR6b and FcR7) had higher residual activity than the wild type Fc-binding protein, confirming that the acid stability was increased with the variant Fc-binding proteins.

TABLE 9

| | Fc binding protein | | Residual activity |
|---|---|---|---|
| | Designation | SEQ ID NO: | (%) |
| Example 3 | FcR2 | 27 | 27.2 |
| Example 4 (a) | FcR3 | 31 | 57.1 |
| Example 4 (b) | FcR4 | 33 | 76.4 |
| Example 4 (c) | FcR5a | 37 | 85.9 |
| Example 4 (d) | FcR5b | 41 | 71.4 |
| Example 4 (e) | FcR6a | 43 | 89.8 |
| Example 4 (f) | FcR6b | 47 | 76.4 |
| Example 4 (g) | FcR7 | 49 | 84.6 |
| Example 1 | Wild type | 25 | 14.5 |

Example 7

Construction of Fc-Binding Protein with One Amino Acid Substitution

Among the amino acid substitutions associated with increased stability of Fc-binding protein as demonstrated in Example 3, Fc-binding proteins having valine (Val) at position 27, tyrosine (Tyr) at position 35 and glutamic acid (Glu) at position 121 of SEQ ID NO: 1 substituted with other amino acids were constructed by the following methods.

(A) Construction of Fc-binding protein with valine (Val) at position 27 of SEQ ID NO: 1 substituted with other amino acids.

(A-1) PCR was conducted by the same method as Example 4 (a-1), except that the pET-eFcR constructed in Example 1 was used as template and oligonucleotides comprising the sequences of SEQ ID NO: 24 and SEQ ID NO: 51 (5'-CTGCCGAAAGCGNNKGIGTTTCTGGAACCG-3') were used as PCR primers. The purified. PCR product was designated as 27 pF.

(A-2) PCR was conducted by the same method as Example 4 (a-1), except that the pET-eFcR constructed in Example 1 was used as template and oligonucleotides comprising the sequences of SEQ ID NO: 23 and SEQ ID NO: 52 (5'-TTCCAGAAACACMNNCGCTTTCGGCAGATC-3') were used as PCR primers. The purified. PCR product was designated as 27p R.

(A-3) After mixing the two PCR products obtained in (A-1) and (A-2) (27pF and 27pR), PCR was conducted in the same manner as Example 4 (a-3), and 27pF and 27pR were linked. The obtained PCR product was designated as 27p.

(A-4) PCR was conducted by the same method as Example 4 (a-4), except that the PCR product 27p obtained in (A-3) was used as template, and oligonucleotides comprising the sequences of SEQ ID NO: 23 and SEQ ID NO: 24 were used as PCR primers. Thus were constructed polynucleotides coding for Fc-binding proteins having valine at position 27 of SEQ ID NO: 1 substituted with different amino acids.

(A-5) The polynucleotide obtained in (A-4) was purified and then digested with restriction enzymes NcoI and HindIII and ligated with the expression vector pETMalE that had been previously digested with restriction enzymes NcoI and HindIII (Japanese Unexamined Patent Publication No. 2011-206046), and the ligation product was used for transformation of E. coli BL21 (DE3).

(A-6) The obtained transformants were cultured on LB medium containing 50 μg/mL kanamycin. The plasmids were extracted from the harvested cells (transformants), and the nucleotide sequences were analyzed by the same method as Example 1 (5).

As a result, there were obtained polynucleotides coding for Fc-binding proteins having the amino acid substitutions Val27Gly (V27G), Val27Lys (V27K), Val27Thr Val27Ala (V27A), Val27Trp (V27W) and Val27Arg W27R).

(B) Construction of Fc-binding protein with tyrosine (Tyr) at position 35 of SEQ ID NO: 1 substituted with other amino acids.

(B-1) PCR was conducted by the same method as Example 4 (a-1), except that the pET-eFcR constructed in Example 1 was used as template and oligonucleotides comprising the sequences of SEQ ID NO: 24 and SEQ ID NO:53 (5'-AACCGCAGTGGNNKCGCGTGCTGGAGAAAG-3') were used as PCR primers. The purified PCR product was designated as 35 pF.

(B-2) PCR was conducted by the same method as Example 4 (a-1), except that the pET-eFcR constructed in Example 1 was used as template and oligonucleotides comprising the sequences of SEQ ID NO: 23 and SEQ ID NO: 54 (5'-AGCACGCGMNNCCACTGCGGTTCCAGAAAC-3') were used as PCR primers. The purified. PCR product was designated as 35pR.

(B-3) After mixing the two PCR products obtained in (B-1) and (B-2) (35pF and 35pR), PCR was conducted in the same manner as Example 4 (a-3), and 35pF and 35pR were linked. The obtained PCR product was designated as 35p.

(B-4) PCR was conducted by the same method as Example 4 (a-4), except that the PCR product 35p obtained in (B-3) was used as template, and oligonucleotides comprising the sequences of SEQ ID NO: 23 and SEQ ID NO: 24 were used as PCR primers. Thus were constructed polynucleotides coding for Fc-binding proteins having tyrosine at position 35 of SEQ ID NO: 1 substituted with different amino acids.

(B-5) The polynucleotide obtained in (B-4) was purified and then digested with restriction enzymes NcoI and HindIII and ligated with the expression vector pETMalE previously digested with restriction enzymes NcoI and HindIII (Japanese Unexamined Patent Publication No. 2011-206046), and the ligation product was used for transformation of E. coli BL21 (DE3).

(B-6) The obtained transformants were cultured on LB medium containing 50 μg/mL kanamycin. The plasmids were extracted from the harvested cells (transformants), and the nucleotide sequences were analyzed by the same method as Example 1 (5).

As a result there were obtained polynucleotides coding for Fc-binding proteins having the amino acid substitutions Tyr35Cys (Y35C), Tyr35Asp (Y35D), Tyr35Phe (Y35F), Tyr35Gly (Y35G), Tyr35Lys (Y35K), Tyr35Leu (Y35 L), Tyr35Asn (Y35N), Tyr35Pro (Y35P), Tyr35Arg (Y35R), Tr35Ser (Y35S), Tyr35Thr (Y35T), Tyr35Val (Y35V) and Tyr35Trp (35W).

(C) Construction of Fc-binding protein with glutamic acid (Glu) at position 121 of SEQ ID NO: 1 substituted with other amino acids.

(C-1) PCR was conducted by the same method as Example 4 (a-1), except that pET-eFcR constructed in Example 1 was used as template and oligonucleotides comprising the sequences of SEQ ID NO: 24 and SEQ ID NO: 5 (5'-GTGITCAAAGAGNNKGATCCGATTCATCTG-3') were used as PCR primers. The purified. PCR product was designated as 121pF.

PCR was conducted by the same method as Example 4 (a-1), except that pET-eFcR constructed in Example 1 was used as template and oligonucleotides comprising the sequences of SEQ ID NO: 23 and SEQ ID NO: 56 (5'-AATCGGATCMNNCTCTTTGAACACCCACCG-3') were used as PCR primers. The purified. PCR product was designated as 121pR.

(C-3) After mixing the two PCR products obtained in (C-1) and (C-2) (121pF and 121pR), PCR was conducted in the same manner as Example 4 (a-3), and 121pF and 121pR were linked. The obtained PCR product was designated as 121p.

(C-4) PCR was conducted by the same method as Example 4 (a-4), except that the PCR product 121p obtained in (C-3) was used as template, and oligonucleotides comprising the sequences of SEQ ID NO: 23 and SEQ ID NO: 24 were used as PCR primers. Thus were constructed polynucleotides coding for Fc-binding proteins having glutamic acid at position 121 of SEQ ID NO: 1 substituted with different amino acids, (C-5) The polynucleotide obtained in (C-4) was purified and then digested with restriction enzymes NcoI and HindIII and ligated with the expression vector pETMalE that had been digested with restriction enzymes NcoI and HindIII (Japanese Unexamined Patent Publication No. 2011-206046), and the ligation product was used for transformation of E. coli BL21 (DE3).

(C-6) The obtained transformants were cultured on LB medium containing 50 μg/mL kanamycin. The plasmids were extracted from the harvested cells (transformants), and the nucleotide sequences were analyzed by the same method as Example 1 (5).

As a result there were obtained polynucleotides coding for Fc-binding proteins having the amino acid substitutions Glu121Lys (E121K), Glu121Pro (E121P), Glu121Arg (E121R), Glu121Gly (E121G), Glu121His (E121H) and Glu121Val (E121V).

Example 8

Evaluation of Antibody Binding Activities of Fc-Binding Proteins with 1 Amino Acid Substitution (1) Transformants expressing the wild type Fc-binding protein constructed in Example 1 and the Fc-binding proteins with amino acid substitutions at one location constructed in Example 7, were each cultured by the same method described in Example 3 (1) and (2), and the wild type Fc-binding protein and the Fc-binding proteins with 1 amino acid substitution were expressed.

(2) The antibody-binding activity of the expressed Fc-binding proteins with 1 amino acid substitution was examined by the ELISA method described in Example 3 (4).

Figure 2:
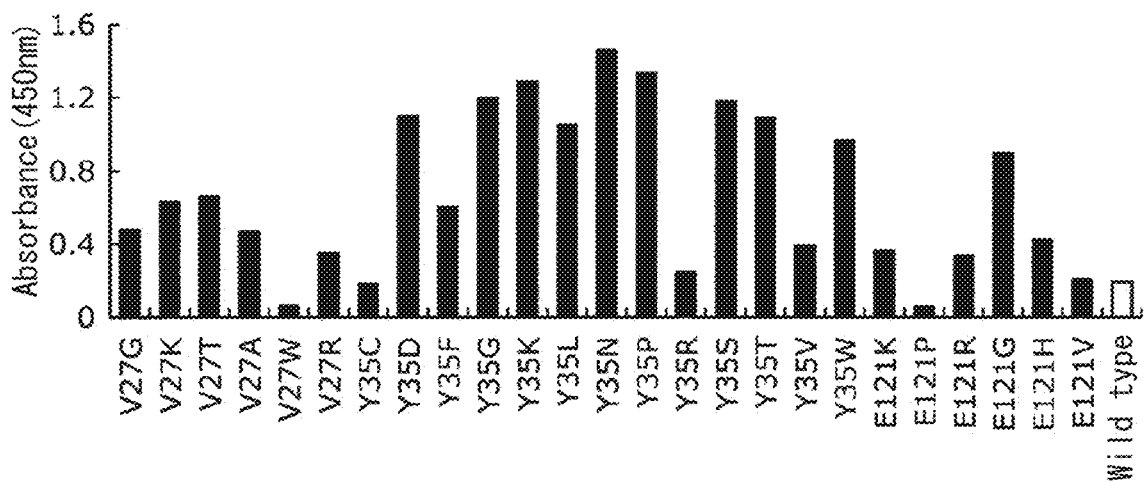
FIG. 2 is a graph showing the results of evaluating the antibody-binding activity of Fc-binding proteins having 1 amino acid substitution. The wild type in the graph is Fc-binding protein without amino acid substitution.

The results are shown in FIG. 2. Substitution of the valine at position 27 of SEQ ID NO: 1 with glycine (V27G), lysine (V27K), threonine (V27T), alanine (V127A) or arginine (V27R) resulted in increased antibody binding activity compared to the wild type Fc-binding protein, whereas substitution of Val at position 27 of SEQ ID NO: 1 with tryptophan (V27W) resulted in reduced antibody binding activity compared to the wild type Fc-binding protein.

Substitution of tyrosine at position 35 of SEQ ID NO: 1 with aspartic acid (Y35D), phenylalanine (Y35F), glycine (Y3SG), lysine (Y35K), leucine (Y35L), asparagine (Y35N), proline (Y35P), serine (Y35S), threonine (Y35T), valine (Y35V) or tryptophan (Y35W) resulted in increased antibody binding activity compared to the wild type Fc-binding protein. Among these, Y35D, Y35G, Y35K, Y35L, Y35N, Y358, Y35S, Y35T and Y35W had greatly increased antibody binding activity compared to the wild type Fc-binding protein. On the other hand, substitution of tyrosine at position 35 of SEQ ID NO: 1 with cysteine (Y35C) or arginine (Y35R) resulted in approximately equal antibody binding activity to the wild type Fc-binding protein.

Substitution of glutamic acid at position 121 of SEQ ID NO: 1 with lysine (E121K), arginine (E121R), glycine (E121G) or histidine (E121H) resulted in increased antibody binding activity compared to the wild type Fc-binding protein. Among these, E121G had greatly increased antibody binding activity compared to the wild type Fc-binding protein. On the other hand, when glutamic acid at position 121 of SEQ ID NO: 1 was substituted with valine (E121V), the antibody binding activity was approximately equal to that of the wild type Fc-binding protein, and when substituted with proline (E121P), the antibody binding activity was reduced compared to the wild type Fc-binding protein.

Example 9

Evaluation of Thermal Stability of Fc-Binding Proteins with 1 Amino Acid Substitution In order to compare the thermal stabilities of the Fc-binding proteins with 1 amino acid substitution that were evaluated in Example 8, heat treatment was carried out by the same method as Example 3 (3) (45° C., 10 minutes), and the remaining activity was calculated.

Figure 3:
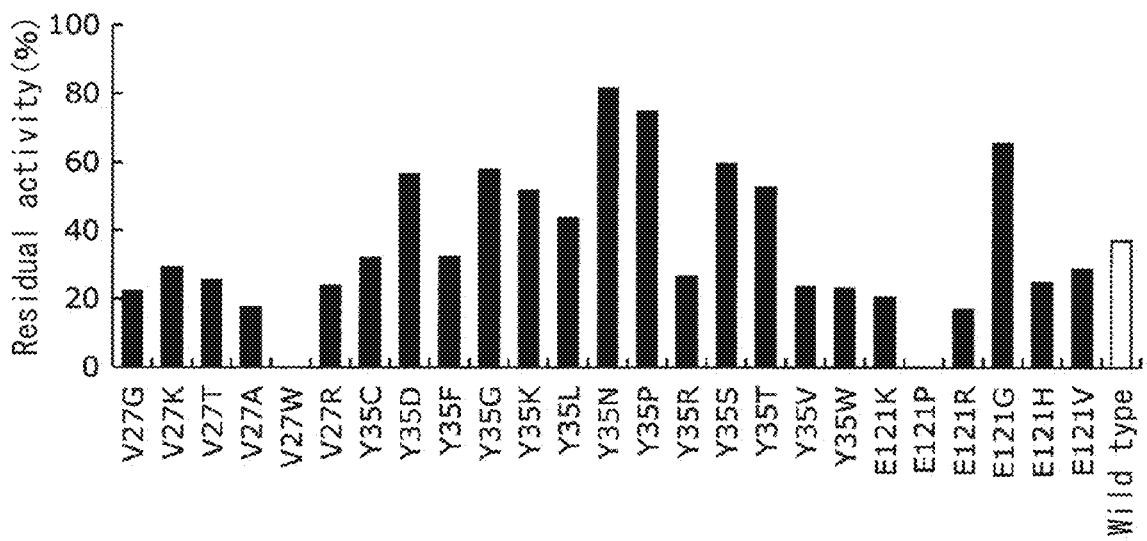
FIG. 3 is a graph showing the results of evaluating the thermal stability of Fc-binding proteins having 1 amino acid substitution. The wild type in the graph is Fc-binding protein without amino acid substitution.

The results are shown in FIG. 3. The Fc-binding proteins wherein tyrosine at position 35 of SEQ ID NO: 1 was substituted with aspartic acid (Y35D), glycine (Y35G), lysine (Y35K), leucine (Y35L), asparagine (Y35N), proline (Y35P), serine (Y35S) or threonine (Y35T), and the Fc-binding proteins wherein glutamic acid at position 121 of SEQ ID NO: 1 was substituted with glycine (E121G), had greatly increased thermal stability compared to the wild type Fc-binding protein. Among these, Y35N and Y35P had greatly increased thermal stability compared to the wild type Fc-binding protein.

Example 10

Large-Volume Preparation of FcR5a (1) Transformants expressing the FcR5a constructed in Example 4 (c) were inoculated into 400 ml of 2YT liquid medium (16 g/L peptone, 10 g/L yeast extract and 5 g/L sodium chloride) containing 50 μg/mL kanamycin in a 2 L baffle flask, and aerobically shake cultured overnight at 37° C., as preculturing.

(2) After inoculating 180 ml of the culture solution of (1) into 1.8 L of liquid medium containing 10 g/L glucose, 20 g/L yeast extract, 3 g/L trisodium phosphate dodecahydrate, 9 g/L disodium hydrogen phosphate dodecahydrate, 1 g/L ammonium chloride and 50 mg/L kanamycin sulfate, a 3 L fermenter (product of Baiotto) was used for main culturing. The conditions were set to a temperature of 30° C., a pH of 6.9 to 7.1, an aeration rate of 1 VVM and a dissolved oxygen concentration at 30% saturated concentration, and main culturing was commenced. For pH regulation, 50% phosphoric acid was used as the acid and 14% ammonia water was used as the alkali, the dissolved oxygen was controlled by varying the agitation speed, and the stirring rotational speed was set with a lower limit of 500 rpm and an upper limit of 1000 rpm. After the start of culturing, and when the glucose concentration was no longer measurable, feeding culture medium (248.9 g/L glucose, 83.3 g/L yeast extract, 7.2 g/L magnesium sulfate heptahydrate) was added while controlling the dissolved oxygen. (DO).

(3) When the absorbance at 600 nm ($OD_{600\ nm}$) reached about 150 as a measure of the cell mass, the culturing temperature was lowered to 25° C. and upon confirming that the preset temperature had been reached, IPTG was added to a final concentration of 0.5 mM and culturing was continued at 25° C.

(4) Culturing was terminated at about 48 hours after the start of culturing, and the cells were recovered by centrifugation of the culture solution at 8000 rpm for 20 minutes at 4° C.

(5) A portion of the cells recovered in (4) were suspended in 20 mM Tris-HCl buffer (pH 7.4) containing 150 mM sodium chloride, to 5 mL/1 g (cells), and an ultrasonic generator (INSONATOR 201M, trade name of Kubota Corp.) was used to disrupt the cells at 4° C. for about 10 minutes, with an output of about 150 W. The cell disruptate was centrifuged twice at 4° C. for 20 minutes, 10,000 rpm, and the supernatant was collected.

(6) After adding imidazole to the disruptate obtained in (5) to a final concentration of 20 mM, it was applied to an XK 26/20 column (product of GE Healthcare) packed with 50 mL, of Ni Sepharose 6 Fast Flow (product of GE Healthcare) previously equilibrated with 20 mM Tris-HCl buffer (pH 7.4) containing 150 mM sodium chloride and 20 mM imidazole. After rinsing with the buffer used for equilibration, 20 mM Tris-HCl buffer (pH 7.4) containing 150 mM sodium chloride and 0.5 M imidazole was used for elution of the FcR5a.

(7) The eluate obtained in (6) was applied to an HR 16/10 column (product of GE Healthcare) packed with 30 ml of IgG Sepharose (product of GE Healthcare) previously equilibrated with 20 mM Tris-HCl buffer (pH 7.4) containing 150 mM sodium chloride. After rinsing with the buffer used for equilibration, the FcR5a was eluted with 0.1 M glycine hydrochloride buffer (pH 3.0). The eluate was restored to nearly neutral pH by addition of 1 M Tris-HCl buffer (pH 7.0) at ¼ the volume of the eluate.

Example 11

Preparation of FcR5a-Immobilizing Gel (1) The FcR5a prepared in Example 10 was concentrated and exchanged with buffer using an ultrafiltration membrane (Amicon Ultra-15, product of Millipore), and then concentrated to 8.37 mg/mL in 20 mM Tris-HCl buffer (pH 7.4) containing 150 mM sodium chloride.

(2) An epoxy Toyopearl gel was prepared by reacting 1,6-hexanediol diglycidyl ether with the hydroxyl groups of a hydrophilic vinyl polymer (Toyopearl, product of Tosoh. Corp.), as the support.

(3) There were prepared h spin columns (product of Bio-Rad Laboratories, Inc.) housing 100 μL of the epoxy Toyopearl gel prepared in (2), and rinsing was performed 3 times with 0.5 mL of 0.1 M borate buffer (pH 9.0) containing 0.5 M sodium chloride.

(4) A solution comprising a mixture of 0.3 mL of the FcR5a solution prepared in (1) and 0.45 mL of 0.1 M borate buffer (pH 9.0) containing 0.5 M sodium chloride was added to each of the spin columns packed with gel described in (3), and shake cultured at 35° C. for 3 hours.

(5) After collecting the mixed solutions of FcR5a solution and 0.1 M borate buffer containing 0.5 M sodium chloride, which had been added to the gel, rinsing was performed 3 times with 0.2 mL of 0.1 M glycine hydrochloride buffer (pH 3.0). Next, the pH was restored to near neutral by rinsing 3 times with 0.5 mL of 20 mM Tris-HCl buffer (pH 7.4) containing 150 mM sodium chloride, and 0.5 mL of FcR5a-immobilizing gel was prepared.

The protein concentrations in the solution collected in (5) and in the rinsing solution were measured, and the amount of FcR5a immobilized on the gel was calculated to determine the immobilization rate, by which it was found that 33.7% of the added FcR5a had been immobilized on the gel.

Example 12

Antibody Separation with FcR5a-Immobilizing Gel (1) After packing 0.5 ml of the FcR5a-immobilizing gel prepared in Example 11 into an HP16/5 column (product of GE Healthcare), it was connected to an AKTAprime plus (product of GE Healthcare). It was then equilibrated with 20 mM Tris-HCl buffer (pH 7.4) containing 150 mM sodium chloride.

(2) The 20 mM Tris-HCl buffer (pH 7.4) containing 150 mM sodium chloride was passed through at a flow rate of 0.1 mL, and then 0.5 ml of a solution of human IgG1 (I5154-1 MG, product of Sigma Corp.) prepared to 1 mg/ml, was applied with 20 mM Tris-HCl buffer (pH 7.4) containing 150 mM sodium chloride, to adsorb the human IgG1 onto the FcR5a-immobilizing gel. This was followed by equilibration by passing through 20 mM acetate buffer (pH 5.0), and the adsorbed human IgG1 was eluted with a pH gradient using 20 mM glycine hydrochloride buffer (pH 3.0). The eluted human IgG1 was recovered in 0.5 mL fractions.

The elution pattern and recovered fractions of the human IgG1 are shown in FIG. 4. Of the recovered elution fractions, a mixture of fraction 13 (Fr13) and fraction 14 (Fr14) was used as fraction A (FrA), and a mixture of fraction 16 (Fr16) and fraction 17 (Fr17) was used as fraction B (FrB).

Example 13

Sugar Chain Structure Analysis of Isolated Antibodies (1) After denaturing the pre-purification human IgG1 and elution fractions (FrA and FrB) used in Example 12, by heat treatment at 100° C. for 10 minutes, they were treated with glycoamidase A/pepsin and pronase in that order, and subjected to a purification procedure by gel filtration to obtain the sugar chain fraction.

(2) The sugar chains obtained in (1) were concentrated and dried with an evaporator, and then reacted with 2-aminopyridine and dimethylamineborane in that order, in an acetic acid solvent to obtain fluorescent-labeled sugar chains, which were purified by gel filtration.

(3) The fluorescent-labeled sugar chains obtained in (2) were separated into a neutral sugar chain fraction and a monosialylated sugar chain fraction, using an anion exchange column (TSKgel DEAF-5PW, φ7.5 mm×7.5 cm, product of Tosoh Corp.).

(4) The neutral sugar chain fraction and monosialylated sugar chain fraction obtained in (3) were isolated into individual sugar chains using an ODS column. After obtaining molecular weight information for the isolated sugar chains by MALDI-TOF-MS analysis, the sugar chain structures were assigned taking into account the retention time of the ODS column chromatograph.

The compositional ratios of the neutral sugar chains are shown in Table 10, and the compositional ratios of the monosialylated sugar chains are shown in Table 11. The assigned sugar chain structures (N1 to N8 and M1 and M2) are shown in FIG. 5. Based on the results shown in Table 10, antibodies having the sugar chain structures N2 and N7 were detected before purification and with FrB, but were not detected from FrA. That is, since the antibodies having the aforementioned two different sugar chain structures (N2 and N7 in FIG. 5) were not detected in the early eluted fraction. FrA but were detected in the late eluted fraction FrB, this suggested that they were strongly bound to the FcR5a-immobilizing gel, compared to antibodies with other sugar chain structures. The results demonstrated that the FcR5a-immobilizing gel, as one mode of the adsorbent of the invention, can separate antibodies based on the sugar chain structures of the antibodies.

TABLE 10

| Structure designation in FIG. 5 | Pre-purification sugar chains (compositional ratio %) | FrA (compositional ratio %) | FrB (compositional ratio %) |
| --- | --- | --- | --- |
| N1 | 3.7 | 16.7 | 2.7 |
| N2 | 2.1 | Not detected | 2.0 |
| N3 | 21.8 | 14.6 | 13.6 |
| N4 | 39.1 | 29.2 | 37.2 |
| N5 | 10.2 | 8.3 | 10.9 |
| N6 | 15.5 | 20.8 | 19.6 |
| N7 | 1.9 | Not detected | 2.2 |
| N8 | 5.8 | 10.4 | 11.7 |

TABLE 11

| Structure designation in FIG. 5 | Pre-purification sugar chains (compositional ratio %) | FrA (compositional ratio %) | FrB (compositional ratio %) |
| --- | --- | --- | --- |
| M1 | 25.1 | 26.7 | 25.0 |
| M2 | 74.9 | 73.3 | 75.0 |

Example 14

Antibody Purification with FcR5a-Immobilizing Gel

The FcR5a-immobilizing gel prepared in Example 11 was used for purification of human IgG1 and human IgG3.

(1) A 0.2 mL portion of FcR5a-immobilizing gel was prepared by the same method as Example 11. A 0.1 mL portion of the prepared FcR5a-immobilizing gel was packed into a spin column.

(2) The column packed with the FcR5a-immobilizing gel prepared in (1) was rinsed 3 times with 0.5 mL of 20 mM Tris-HCl buffer (pH 7.4) containing 150 mM sodium chloride.

(3) A model culture solution was prepared by adding human IgG1 (I5154-1 MG, product of Sigma) or human IgG3 (14639-1 MG, product of Sigma) at 0.3 mg/mL to culture medium containing 10% fetal calf serum (FCS) added to DMEM/F12 culture medium (Life Technologies) as a medium for animal cells.

(4) The model culture solution prepared in (3) was added at 0.4 ml to the column rinsed in (2), and was shaken at 25° C. for 2 hours.

(5) The model culture solution was removed and rinsed 4 times with 0.5 mL of 20 mM Tris-HCl buffer (pH 7.4) containing 150 mM sodium chloride, and then eluted with 500 µL of 0.1 M glycine hydrochloride buffer (pH 3.0), recovering 100 µL fractions.

(6) The model culture solution and elution fractions were each heat treated with addition of 2× sample buffer (50 mM Tris-HCl buffer (pH 6.8) containing 2 (w/v) % sodium dodecyl sulfate, 6 (w/v) % β-mercaptoethanol, 10 (w/v) % glycerin and 0.005 (w/v) % bromophenol blue). Next, each treated sample was separated by electrophoresis using a 5-20% gradient SDS-PAGE gel (by Atto Corp.). For comparison, human IgG1 and human IgG3 added to the model culture solution (concentration: 0.2 mg/mL) were also treated in the same manner and analyzed by SDS-PAGE.

Figure 6:
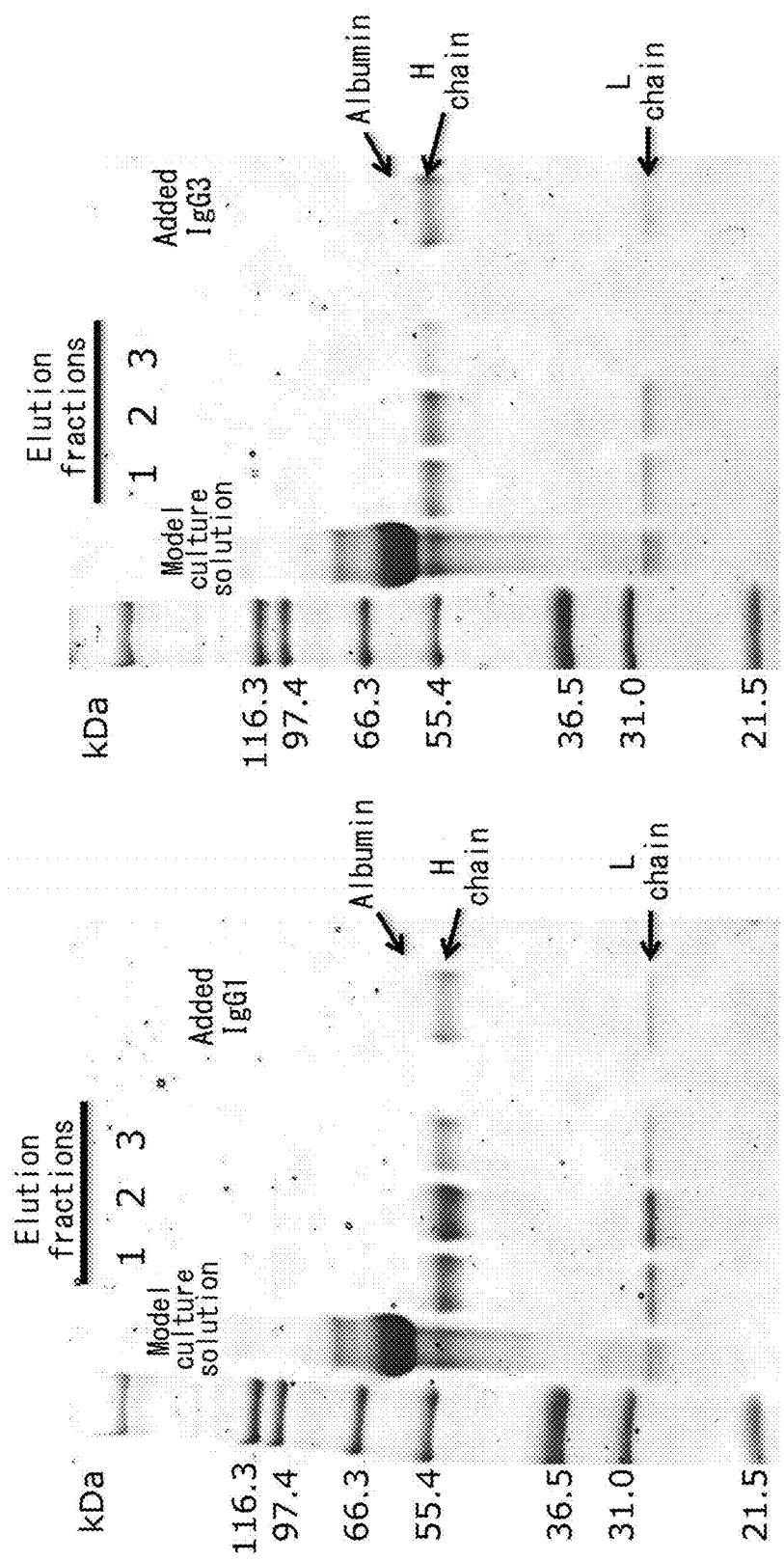
FIG. 6 is a pair of photographs (SDS-PAGE) showing results of antibody purification using FcR5a-immobilizing gel. (A) shows the results for purification of human IgG1, and (B) shows the results for purification of human IgG3.

FIG. 6 shows the SDS-PAGE analysis results for the elution fractions containing human IgG1 and human IgG3. Since the elution fraction containing human IgG1, obtained by purifying the human IgG1-added model culture solution, was at the same location as human IgG1 added to the model culture solution, and no band was observed for albumin as was observed in the model culture solution, this confirmed that the human IgG1 had been purified to a high degree of purity (FIG. 6(A)). Moreover, since the elution fraction containing human IgG3, obtained by purifying the human IgG3-added model culture solution, was also at the same location as human IgG3 added to the model culture solution, and no band was observed for albumin as was observed in the model culture solution, this confirmed that the human IgG3 had been purified to a high degree of purity (FIG. 6(B)). These results demonstrated that the FcR5a-immobilizing gel, as a mode of the adsorbent of the invention, can purify human IgG1 and human IgG3 from animal cell culturing solution.

Example 15

Preparation of Sugar Chain-Removed Human IgG1

The N-linked sugar chains were removed from human IgG1 by the method described below.

(1) Human IgG1 (31-AI17, product of Fitzgerald) was diluted with 20 mM Tris-HCl buffer (pH 7.4) containing 150 mM sodium chloride, to a concentration of 3 mg/mL.

(2) After adding 100 µL of 1 M Tris-HCl buffer (pH 8.6) to 100 µL of the diluted solution of (1), 10 µL of N-glycosidase F (500 mU/µL, 4450, product of Takara Bio, Inc.) was added, and then the mixture was allowed to stand at 37° C. for 24 hours to remove the N-linked sugar chains of the IgG1.

(3) The treatment solution of (2) was applied to an open column (product Bio-Rad Laboratories, Inc.) packed with 100 µL of Toyopearl AF-rProtein A-650F (22803, product of Tosoh Corp.) that had been previously equilibrated with 20 mM Tris-HCl buffer (pH 7.4) containing 150 mM sodium chloride.

(4) After rinsing 3 times with 500 µL of 20 mM Tris-HCl buffer (pH 7.4) containing 150 mM sodium chloride, elution was performed 7 times with 100 µL of 0.1 N glycine hydrochloride buffer (pH 3.0), for purification of the N-linked sugar chain-removed human IgG (hereunder referred to simply as "sugar chain-removed human IgG1"). The eluate was neutralized by adding 1 M Tris-HCl buffer (pH 8.0) at ¼ the volume of the eluate.

(5) To the sugar chain-removed human IgG solution obtained in (4) there was added an equivalent of sample buffer (50 mM Tris-HCl buffer (pH 6.8) containing 2 (w/v) % sodium dodecyl sulfate, 6 (w/v) β-mercaptoethanol, 10 (w/v) % glycerin and 0.005 (w/v) % bromophenol blue), and heat treatment was performed for reduction of the sugar chain-removed human IgG1.

(6) The human IgG1 was separated by electrophoresis using a 5-20% gradient SDS-PAGE gel (by Atto Corp.). For comparison, an aqueous solution of human IgG1 without sugar chain treatment. (hereunder referred to as "sugar chain-bearing human IgG1") (concentration: 0.5 mg/mL) was also subjected to reduction treatment in the same manner as (5), and separated by SDS-PAGE.

Figure 7:
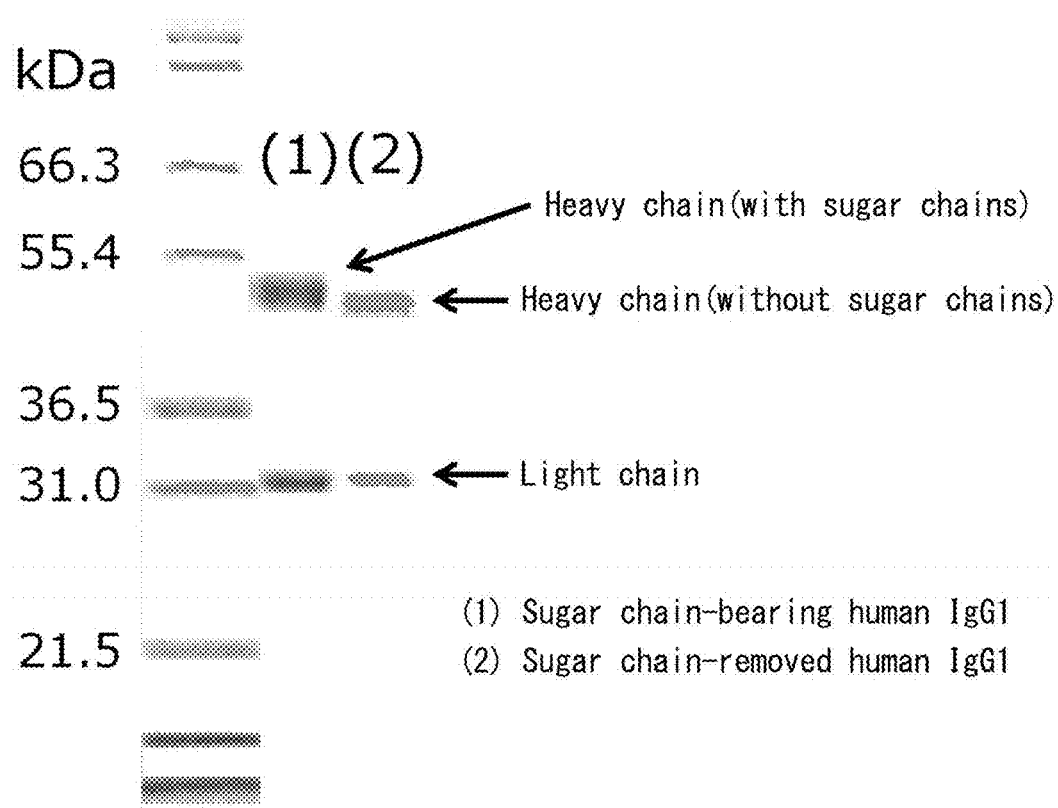
FIG. 7 is an image showing a molecular weight comparison between human. IgG1 with sugar chains (sugar chain-bearing human IgG1) and human IgG1 with the sugar chains removed (sugar chain-removed human. IgG1) by SDS-PAGE. Lane (1) in the image represents sugar chain-bearing human. IgG1, and lane (2) is sugar chain-removed human IgG1.

The results are shown in FIG. 7. Because the heavy chains of the sugar chain-removed human IgG1 had the N-linked sugar chains removed, they were of lower molecular weight than the heavy chains of the sugar chain-hearing human. IgG1, and this was confirmed by SDS-PAGE (see lane (2) in FIG. 7). That is, the method of this example allowed confirmation that it is possible to prepare human IgG1 with the N-linked sugar chains removed.

Example 16

Large-Volume Preparation of Human FcγRIIIa (1) Transformants capable of expressing the human FcγRIIIa obtained in Example 1 were inoculated into 400 mL of 2YT liquid medium (16 g/L peptone, 10 g/L yeast extract and 5 g/L sodium chloride) containing 50 µg/mL kanamycin in a 2 L baffle flask, and aerobically shake cultured overnight at 37° C., as preculturing.

(2) After inoculating 180 mL of the preculture solution of (1) into 1.8 L of liquid medium containing 10 g/L glucose, 20 g/L yeast extract, 3 g/L trisodium phosphate dodecahydrate, 9 g/L disodium hydrogenphosphate dodecahydrate, 1 g/L ammonium chloride and 50 mg/L kanamycin sulfate, a 3 L fermenter was used for main culturing. The conditions were set to a temperature of 30° C., a pH of 6.9 to 7.1, an aeration rate of 1 VVM and a dissolved oxygen concentration at 30% saturated concentration, and main culturing was commenced. For pH regulation, 50% phosphoric acid was used as the acid and 14% ammonia water was used as the alkali, the dissolved oxygen was controlled by varying the agitation speed, and the agitation rotational speed was set with a lower limit of 500 rpm and an upper limit of 1000 rpm. After the start of culturing, and when the glucose concentration was no longer measurable, feeding culture medium (248.9 g/L glucose, 63.3 g/L yeast extract, 7.2 g/L magnesium sulfate heptahydrate) was added while controlling the dissolved oxygen (DO).

(3) When the absorbance at 600 nm ($OD_{600\ nm}$) reached about 150 as a measure of the cell mass, the culturing temperature was lowered to 25° C., and upon confirming that the preset temperature had been reached, IPTG (isopropyl-β-thiogalactopyranoside) was added to a final concentration of 0.5 mM and culturing was continued at 25° C.

(1) Culturing was terminated at about 48 hours after the start of culturing, and the cells were harvested by centrifugation of the culture solution at 8000 rpm for 20 minutes.

(5) The cells harvested in (4) were suspended in 20 mM Tris-HCl buffer (pH 7.4) containing 150 mM sodium chloride, to 5 mL/1 g (cells), and an ultrasonic generator (IN-SONATOR 201M, trade name of Kubota Corp.) was used to disrupt the cells at 4° C. for about 10 minutes, with an output of about 150W. The cell disruptate was centrifuged twice at 4° C. for 20 minutes, 10,000 rpm, and the supernatant was collected.

(6) After adding imidazole to the disruptate obtained in (5) to a final concentration of 20 mM, it was applied to an XK 26/20 column (product of GE Healthcare) packed with 50 mL of Ni Sepharose 6 Fast Flow (product of GE Healthcare) previously equilibrated with 20 mM Tris-HCl buffer (pH 7.4) containing 150 mM sodium chloride and 20 mM imidazole.

(7) After rinsing with the buffer used for equilibration, 20 mM Tris-HCl buffer (pH 7.4) containing 150 mM sodium chloride and 0.5 M imidazole was used for elution of the human FcγRIIIa.

(8) The eluate obtained in (7) was applied to an HR 16/10 column (product of GE Healthcare) packed with 10 mL of IgG Sepharose (product of GE Healthcare) previously equilibrated with 20 mM Tris-HCl buffer (pH 7.4) containing 150 mM sodium chloride. After rinsing with the buffer used for equilibration, the human FcγRIIIa was eluted with 0.1 M glycine hydrochloride buffer (pH 3.0). The eluate was restored to nearly neutral pH by addition of 1 M Tris-HCl buffer (pH 8.0) at ¼ the volume of the eluate.

Example 17

Measurement of Affinity of Human FcγRIIIa for Antibodies (1) The human FcγRIIIa prepared in Example 16 was dialyzed against phosphate buffer (buffer at pH 7.4 containing 137 mM NaCl, 8.1 M $Na_2HPO_4$, 2.68 mM KCl and 1.47 mid $KH_2PO_4$) for buffer exchange, and the concentration of the human FcγRIIIa was measured from the absorbance at 280 nm.

(2) After diluting the human FcγRIIIa whose concentration was measured in (1), to 10 µg/mL using 20 mM acetate buffer (pH 5.5), an amine coupling kit (product of GE Healthcare) was used for immobilization on a sensor chip CM5 (product of GE Healthcare), and a Biacore T-100 (product of GE Healthcare) was used to measure the amount of human FcγRIIIa immobilized. As a result, the amount of human. FcγRIIIa immobilized was found to be 488.2 RU (1 RU=1 pg/mm²). In addition, Protein A (product of ProteNova Co., Ltd.) was diluted to 10 µg/mL with 20 mM acetate buffer (pH 5.5) in the same manner and immobilized on CM5 (product of GE Healthcare). The result of measurement of the amount immobilized with Biacore T-100 was an immobilization amount of 290.0 RU.

(3) The sugar chain-bearing human IgG1 and the sugar chain-removed human IgG1 prepared in Example 15 were diluted to 128 µg/mL, 64 µg/mL, 32 µg/mL, 16 µg/mL, 8 µg/mL, 4 µg/mL, 2 µg/ml, and 1 µg/mL using HBS-EP(+)

(solution at pH 7.4, containing 10 mM HEPES, 150 mM MaCl, 3 mM EDTA and 0.005 (v/v) Surfactant 920 (product of GE Healthcare)).

(4) Using the protein-immobilizing chips prepared in (2), sugar chain-bearing human IgG1 or sugar chain-removed human IgG1 in amounts of 4 µg/ml, to 128 µg/mL were passed through at a flow rate of 30 µL/min, for the human FcγRIIIa-immobilizing chip, and sugar chain-bearing human. IgG1 or sugar chain-removed human IgG1 was passed through in amounts of 1 µg/mL to 16 µg/mL at a flow rate of 30 µL/min, for the Protein A-immobilizing chip, to cause binding between the human IgG1 and the proteins immobilized on the chips, and measurement was performed with Biacore 1-100 under conditions with a contact time of 210 seconds and a dissociation time of 400 seconds, to measure the affinity between the human IgG1 and the proteins immobilized on the chips.

The measurement results are shown in FIG. 8. It is seen that human FcγRIIIa has affinity for sugar chain-bearing human IgG1, but binds very weakly to sugar chain-removed human IgG1 (see FIG. 8(A)). In other words, these results indicate that human FcγRIIIa recognizes differences in sugar chain addition on antibodies. It is also seen, on the other hand, that Protein A has the same affinity for human IgG1, both with and without sugar chains (see FIG. 8(B)).

Example 18

Preparation of Human FcγRIIIa-Immoblizing Gel (1) The human FcγRIIIa prepared in Example 16 was concentrated and exchanged with buffer using an ultrafiltration membrane (Amicon Ultra-15, product of Millipore), and then concentrated to 2.6 mg/mL in 20 mM Tris-HCl buffer (pH 7.4) containing 150 mM sodium chloride.

(2) An epoxy Toyopearl gel was prepared by reacting 1,6-hexanediol diglycidyl ether with the hydroxyl groups of a hydrophilic vinyl polymer (Toyopearl, product of Tosoh Corp.), as the support.

(3) A 70 µL portion of the epoxy Toyopearl gel prepared in (2) was introduced into a spin column (Bio-Rad Laboratories, Inc.), and rinsing was performed 3 times with 0.5 mL of 0.1 M borate buffer (pH 9.0) containing 0.5 M sodium chloride.

(4) A solution comprising a mixture of 0.4 mL of the human FcγRIIIa solution prepared in (1) and 0.6 mL of 0.1 M borate buffer (pH 9.0) containing 0.5 M sodium chloride was added to the gel of (2), and shaken at 35° C. for 3 hours.

(5) After rinsing the gel prepared in (4) 3 times with 0.2 ml of 0.1 M glycine hydrochloride buffer (pH 3.0), the pH was restored to near neutral by rinsing 3 times with 0.5 ml of 20 mM Tris-HCl buffer (pH 7.4) containing 150 mM sodium chloride, and 0.2 ml of human FcγRIIIa-immobilizing gel was prepared.

(6) The protein concentrations in the solution added to the gel of (2) and in the rinsing solution were measured, and the amount of human FcγRIIIa immobilized on the gel was calculated to determine the immobilization rate, by which it was found that 84% of the added human FcγRIIIa had been immobilized on the gel.

Example 19

Isolation of Antibody Using Human FcγRIIIa-Immobilizing Gel (1) The human FcγRIIIa-immobilizing gel prepared in Example 18 was packed into an HR16/5 column (product of GE Healthcare), and the column was connected to an AKTAprime liquid chromatography apparatus (product of GE Healthcare).

(2) The column prepared in (1) was equilibrated with 20 mM Tris-HCl buffer (pH 7.4) containing 150 mM sodium chloride, and human IgG1 (31-AI17, product of Fitzgerald) or the sugar chain-removed human IgG1 prepared in Example 2 (both with solution concentrations of 1 mg/mL) was added at 0.1 mL at a flow rate of 0.1 mL/min. After rinsing with the buffer used for equilibration, elution was performed with 0.1 N glycine hydrochloride buffer (pH 3.5).

Figure 9:
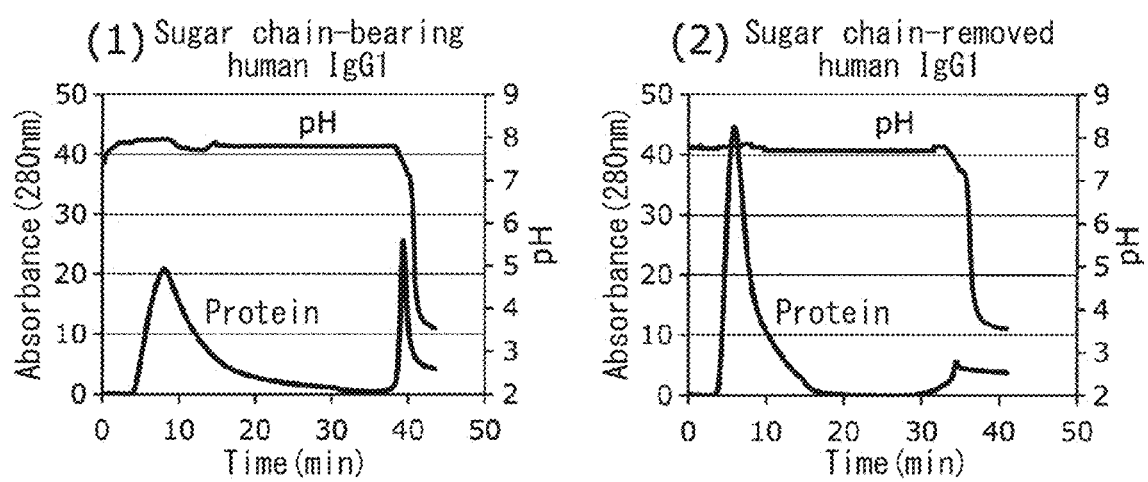
FIG. 9 shows the results of separating sugar chain-bearing human IgG1 and sugar chain-removed human IgG1 with an adsorbent of the invention. (1) shows the results for sugar chain-hearing human IgG1, and (2) shows the results for sugar chain-removed human IgG1.

The results are shown in FIG. 9. It can be seen that, despite flowthrough of the same amount of IgG1, the sugar chain-removed human IgG1 (see FIG. 9(2)) resulted in a greater amount of antibody flow through without being adsorbed on the gel, compared to the sugar chain-bearing human IgG1 (see FIG. 9(1)). Moreover, with the sugar chain-bearing human IgG1, antibody eluted when 0.1 M glycine-hydrochloride buffer (pH 3.5) was added (see FIG. 9(1)), whereas with the sugar chain-removed human IgG1 there was virtually no adsorption onto the gel and no antibody eluted (see FIG. 9(2)). In other words, an adsorbent obtained by immobilizing human FcγRIIIa onto an insoluble support has the ability to specifically adsorb an antibody with sugar chains, and this ability can be utilized to identify whether or not sugar chain addition is present on the antibody.

INDUSTRIAL APPLICABILITY

The adsorbent of the invention specifically adsorbs antibodies with sugar chains and can therefore isolate and purify antibodies with sugar chains to a high degree of purity. The adsorbent of the invention can therefore be utilized for antibody drug production and for quality control.

The invention claimed is:

1. An Fc-binding protein comprising the amino acid residues from position 17 to position 192 of the amino acid sequence of SEQ ID NO: 1, wherein one of the following (1) to (10) amino acid substitutions occurs in the amino acid residues from position 17 to position 192:
   (1) A substitution of aspartic acid, asparagine, glycine, lysine, leucine, proline, serine, or threonine for tyrosine at position 35 of SEQ ID NO: 1;
   (2) A substitution of glutamic acid for valine at position 27 of SEQ ID NO: 1 and a substitution of asparagine for tyrosine at position 35 of SEQ ID NO: 1;
   (3) A substitution of glutamine for leucine at position 30 of SEQ ID NO: 1 and a substitution of asparagine for tyrosine at position 35 of SEQ ID NO: 1;
   (4) A substitution of histidine for tyrosine at position 35 of SEQ ID NO: 1 and a substitution of aspartic acid for glutamic acid at position 54 of SEQ ID NO: 1;
   (5) A substitution of histidine for tyrosine at position 35 of SEQ ID NO: 1 and a substitution of threonine for serine at position 155 of SEQ ID NO: 1;
   (6) A substitution of asparagine for tyrosine at position 35 of SEQ ID NO: 1 and a substitution of glycine for serine at position 169 of SEQ ID NO: 1;
   (7) A substitution of asparagine for tyrosine at position 35 of SEQ ID NO: 1, a substitution of leucine for glutamine at position 48 of SEQ ID NO: 1, and a substitution of glutamine for leucine at position 110 of SEQ ID NO: 1;
   (8) A substitution of serine for tyrosine at position 35 of SEQ ID NO: 1, a substitution of tyrosine for phenylalanine at position 151 of SEQ ID NO: 1, and a substitution of glycine for serine at position 167 of SEQ ID NO: 1;
   (9) A substitution of asparagine for tyrosine at position 35 of SEQ ID NO: 1, a substitution of valine for glutamic acid at position 120 of SEQ ID NO: 1, and a substitution of lysine for glutamine at position 192 of SEQ ID NO: 1; and
   (10) A substitution of aspartic acid for tyrosine at position 35 of SEQ ID NO: 1, a substitution of glycine for glutamic acid at position 54 of SEQ ID NO: 1, a substitution of valine for aspartic acid at position 82 of SEQ ID NO: 1, and a substitution of glutamic acid for lysine at position 119 of SEQ ID NO: 1.

2. The Fc-binding protein according to claim 1 (1), wherein tyrosine at position 35 of SEQ ID NO: 1 is substituted with aspartic acid, glycine, lysine, leucine, proline, serine, or threonine.

3. An Fc-binding protein comprising the amino acid residues from position 17 to position 192 of the amino acid sequence of SEQ ID NO: 1, wherein the Fc-binding protein comprises at least one amino acid substitution of tyrosine at position 35 with asparagine.

4. The Fc-binding protein according to claim 3, wherein at least valine at position 27 is substituted with glutamic acid.

5. The Fc-binding protein according to claim 4, wherein the Fc-binding protein comprises the amino acid sequences selected from the group consisting of SEQ ID NO: 27, SEQ ID NO: 31, SEQ ID NO: 33, SEQ ID NO: 37, SEQ ID NO: 41, SEQ ID NO: 43, SEQ ID NO: 47, and SEQ ID NO: 49.

6. The Fc-binding protein according to claim 5, consisting of the amino acid sequence of any one selected from SEQ ID NO: 27, SEQ ID NO: 31, SEQ ID NO: 33, SEQ ID NO: 37, SEQ ID NO: 41, SEQ ID NO: 43, SEQ ID NO: 47, and SEQ ID NO: 49.

7. An adsorbent comprising the Fc-binding protein according to claim 3 and an insoluble support, the Fc-binding protein being immobilized on the insoluble support.

8. A polynucleotide coding for the Fc-binding protein according to claim 1.

9. An expression vector including the polynucleotide according to claim 8.

10. A transformant comprising a host and the expression vector according to claim 9, the host expressing the expression vector.

11. The transformant according to claim 10, wherein the host is *E. coli*.

12. A method for producing an Fc-binding protein, wherein the Fc-binding protein is expressed by culturing the transformant according to claim 10 to obtain an expressed Fc-binding protein, and the expressed Fc-binding protein is recovered from the cultured product.

13. An adsorbent comprising the Fc-binding protein according to claim 2 and an insoluble support, the Fc-binding protein being immobilized on the insoluble support.

14. An adsorbent comprising the Fc-binding protein according to claim 1 and an insoluble support, the Fc-binding protein being immobilized on the insoluble support.

15. An adsorbent comprising the Fc-binding protein according to claim 4 and an insoluble support, the Fc-binding protein being immobilized on the insoluble support.

16. An adsorbent comprising the Fc-binding protein according to claim 5 and an insoluble support, the Fc-binding protein being immobilized on the insoluble support.

17. An adsorbent comprising the Fc-binding protein according to claim 6 and an insoluble support, the Fc-binding protein being immobilized on the insoluble support.

* * * * *